(12) United States Patent
Jackson et al.

(10) Patent No.: US 7,923,552 B2
(45) Date of Patent: Apr. 12, 2011

(54) HIGH YIELD METHOD OF PRODUCING PURE REBAUDIOSIDE A

(75) Inventors: Mel Clinton Jackson, Honolulu, HI (US); Gordon James Francis, Issaquah, WA (US); Robert Gordon Chase, Reno, NV (US)

(73) Assignee: SGF Holdings, LLC, Bellingham, WA (US)

( * ) Notice: Subject to any disclaimer, the term of this patent is extended or adjusted under 35 U.S.C. 154(b) by 1314 days.

(21) Appl. No.: 11/252,430

(22) Filed: Oct. 17, 2005

(65) Prior Publication Data

US 2006/0083838 A1    Apr. 20, 2006

Related U.S. Application Data

(60) Provisional application No. 60/620,280, filed on Oct. 18, 2004, provisional application No. 60/678,653, filed on May 6, 2005.

(51) Int. Cl.
*C07H 1/00* (2006.01)
*C08B 37/00* (2006.01)

(52) U.S. Cl. ......... 536/124; 536/4.1; 536/127; 536/128; 514/25

(58) Field of Classification Search .................. 536/124, 536/4.1, 127, 128; 514/25
See application file for complete search history.

(56) References Cited

U.S. PATENT DOCUMENTS 5,962,678 A * 10/1999 Payzant et al. ................ 536/128
2003/0138538 A1    7/2003 Kitazume et al.

FOREIGN PATENT DOCUMENTS

| JP | 56-121454 A1 | 9/1981 |
| JP | 57-86264 A1 | 5/1982 |
| WO | WO00/03046 A1 | 6/2000 |

OTHER PUBLICATIONS

Kolb et al. (Journal of Agricultural Food Chemistry (Oct. 2001) vol. 49, No. 10, pp. 4538-4541).*
Kolb, N., et al. J. Agric. Food Chem 2001, 49, 4538-4541.
Written Opinion of the International Search Authority in PCT/US2005/037766.
International Preliminary Examination Report in PCT/US2005/037766.
Supplementary European Search Report in EP 05810517.2-2114 (PCT/US2005/037766) (5shts) mailed to EP agent on Jun. 5, 2009.
Search and Examination Report in Chilean App. No. 1092-2007 (PCT/US2005/037766) (7 shts), undated, but mailed (on information and belief) to Chilean agent in Sep. 2009 in the U.S. on Sep. 28, 2009. The addition of the NPL document amends the IDS submitted earlier today and is the only difference between the unamended IDS and the instant, amended, IDS. Applicant does not have an English translation of this report.
Supplementary European Search Report in EP 05810517.2-2114 (PCT/US2005/037766) (5 shts) mailed to EP agent on Jun. 5, 2009.

* cited by examiner

*Primary Examiner* — Shaojia Anna Jiang
*Assistant Examiner* — Michael C Henry
(74) *Attorney, Agent, or Firm* — Paradise Patent Services, Inc.; George E. Darby

(57) ABSTRACT

The invention provides a high throughput, high purity, high yield system and method of isolating and purifying rebaudioside A ("Reb A"), with acceptable water solubility for all commercial uses, from commercially available *Stevia rebaudiana* starting material. The invention also provides a means of maximizing yields of 99+% purity Reb A based on the attributes of a given batch of *Stevia* starting material. The Reb A produced by the invention is water soluble, devoid of bitterness heretofore associated with rebaudioside sweeteners, non-caloric, and suitable for use as a reagent and as an ingredient in orally consumed products, e.g., as a sweetener, flavor enhancer, and flavor modifier.

26 Claims, 13 Drawing Sheets

Starting Material Assay, Pt 1

HIGH YIELD METHOD OF PRODUCING PURE REBAUDIOSIDE A

RELATED APPLICATIONS

This application claims the benefit of two provisional patent applications, Ser. No. 60/620,280, filed on Oct. 18, 2004, and Ser. No. 60/678,653, filed on May 6, 2005, in the U.S. Patent and Trademark Office for an invention entitled "High Yield Method of Producing Rebaudioside A".

BACKGROUND OF THE INVENTION

1. Technical Field

The invention is in the technical field of the purification of rebaudioside A (also known herein as "Reb A" and "RA") from crude extracts from the plant *Stevia rebaudiana, L. Bertoni* ("*Stevia*"). Reb A is a diterpene glycoside found, along with many other glycosides, sterebins, and other compounds, in *Stevia* extracts. Reb A is the sweetest tasting (roughly 250 to 450 times the sweetness of sucrose at sweetener concentrations used in comestibles) glycoside in *Stevia* and has enormous commercial potential as a non-caloric sweetener. Generally speaking, the *Stevia* glycosides, except rebaudioside A, have an undesirable aftertaste (some have a bitter aftertaste), which generally limits the use of such non-Reb A glycosides as sweeteners. Moreover, sterebins (a group of diterpene compounds commonly known as "yellow oil") in *Stevia* extracts have an extremely bitter taste, even in minute concentrations. In short, the technical field, and the technical problem, is to isolate, especially at industrial scale, 99+% purity Reb A from crude *Stevia* extract; such purity eliminates the bitterness or off-taste that characterizes all currently available *Stevia* sweeteners.

2. Related Art

The six rebaudiosides (A to F), stevioside (the predominant glycoside in extracts from wild type *Stevia*), dulcosides, and sterebins are difficult to separate in solution. In particular, the six rebaudiosides share the same diterpene skeleton and differ only in glycoside moieties; all but Reb A has some degree of bitter aftertaste. Scores of patents and journal articles describe efforts to produce pure (i.e., 99+% purity) rebaudioside A, but to date no method of producing pure Reb A in the lab, much less in commercial quantities, has been reported. Many of the reported methods of production require the use of ion exchange columns or gases, the economics of which undermine scale-up to the commercial quantities of sweetener required for the beverage, packaged food, baking, candy, personal care product, pharmaceutical, and other industries.

Most methods for extraction and purification of diterpene glycosides from *Stevia* use complicated processing of crude extracts and require high concentrations of rebaudioside A in starting materials, yet have low yields and low purifies (<95%) of rebaudioside A. Some methods use alkanols and/or hydrous alkanols as solvents. For instance, in paragraphs 49 to 53 of U.S. Published Patent Application No. 2003/0138538 A1 of Kitazume, et al., a method is described whereby plants or dried leaves from *Stevia rebaudiana* are processed using methanol, hydrous methanol, or hydrous ethanol (but not using a reflux process) and column purification to produce an extract containing a minimum of 40% rebaudioside A by weight and with a rebaudioside A to stevioside ratio is 1.5:1. In Kitazume's method, if the starting plant material is not 40% rebaudioside A by weight and with a rebaudioside A to stevioside ratio of 1.5:1 ("Kitazume Threshold Purity"), column purification or recrystallization must be used to produce rebaudioside A of sufficient purity needed to support the object of the Kitazume patent application (the substitution on rebaudioside A of β-1,4-galactosyl using a β-1,4-galactosyl transferase enzyme). The preferred starting material in Kitazume is a *Stevia* extract with at least 70% Reb A content. In the Kitazume method, when recrystallization is used to produce rebaudioside A of Kitazume Threshold Purity for the transferase reaction, the *Stevia* extract is dissolved to saturation in a hydrophilic organic solvent, such as methanol or ethanol, with no water in the solvent, and the solution concentrated or cooled, then filtered to collect the precipitate, a higher purity rebaudioside A; process parameters, e.g., heating and cooling rates, filtration specifications, etc., of the purification of Reb A are not disclosed. Kitazume also does not disclose the purity of the Reb A produced by recrystallization, only that recrystallization can be used when the starting material is below Kitazume Threshold Purity. Importantly, in Kitazume, all Reb A material is produced using cation-exchange resin and anion-exchange resin steps (paragraph 50) following any crystallization or recrystallization steps. A Reb A purity higher than 91.3% (Example 3) is not disclosed, nor is the solubility of Kitazume's Reb A disclosed. In fact, Kitazume does not disclose whether the 91.3% purity Reb A used in the Examples was produced using recrystallization or only by column purification. Reb A with 91.3% purity may be acceptable for the transferase reaction, but it is not acceptable for commercial uses in foods and beverages.

U.S. Pat. No. 5,962,678 to Payzant et al., describes a seven-step extraction and purification of Reb A from *Stevia* plant material, including processing through two ion exchange columns and precipitation out of a methanol solution. For purification of Reb A, after removing mixed sweet glycosides from the second ion exchange column with methanol, the collected eluent is dried. Upon refluxing the dried solids in a methanol solution and then cooling the solution, stevioside precipitates and is captured by filtration. The filtrate is then concentrated (presumably by evaporating the solvent) and cooled and rebaudioside A precipitates. The method in Example 5 of Payzant is described as yielding rebaudioside A with purity up to 98.6%. However, using 80% purity Reb A *Stevia* extract as starting material, repeated efforts by the inventors of the present invention to replicate Payzant's purification of Reb A failed; typical results were a Reb A yield of less than 5% by weight and amorphous crystals with a noticeable, bitter aftertaste. Attempts by a third party to replicate Payzant also failed (unpublished data). In attempts to replicate Example 5, precipitation of Reb A did not begin until more than 40 hours after heat was removed from the methanol solution. The Payzant purification method in Example 5 apparently requires Reb A starting material obtained by following the steps in Payzant claim 1 (the seven-step process using methanol) rather than by procuring commercially available *Stevia* extracts. The Payzant method, therefore, is neither generally applicable to *Stevia* extracts nor scaleable to commercial production of Reb A.

In addition to not being replicable, Payzant teaches away from using hydrous solvents. Payzant uses anhydrous methanol as a reflux solvent to purify stevioside. In Example 2, Payzant states, "Since the sweet glycosides were absorbed on to the XAD-7 resin from water, there is water contained within or on the surface of this resin and this water is removed with the methanol. The only reason for going to dryness is to remove this water. If the minor amount of water wasn't there or if it were removed by the some other means, then the methanol could be removed by evaporation to some level and then the sweet glycosides would crystallize from the solution." In Example 3, Payzant states, "By being anhydrous or as free from water as possible the crystalline yield is maximized and the crystallization time is minimized. For example, 0.5% water in the methanol in this initial crystallization will significantly reduce the yield. The Stevioside can be further purified, if desired, by using the purification technique set forth in Example 5 below." In Example 5, Payzant discloses a purification in which a *Stevia* extract containing 90.2% Reb A (in Example 3, however, the final product had 7.9% Reb A content) is refluxed in a solvent of 86.67% methanol and 13.33% water by mass; this procedure is said to yield 98.6% Reb A; heating rate, cooling rate, stirring, and temperatures are not disclosed. Payzant notes that the extract used in Example 5 is "not from Example 4", but elsewhere discloses achieving only 7.9% purity Reb A. Payzant states in Example 5 that including water in the solvent is "a convenience in the laboratory", but "on a commercial scale anhydrous solvent might be more convenient". In Examples 3 and 5, Payzant expressly teaches away from using hydrous alkanol solvents for purification of *Stevia* glycosides. Payzant does not disclose how the 90.2% purity Reb A used in Example 5 was obtained, i.e., the method of improving Reb A purity from 7.9% to 90.2% is not enabled, and therefore Example 5 is not enabled. Payzant also does not disclose the method used to determine the Reb A purities claimed. Under the Reb A reference standards currently available from Chromadex (www.chromadex.com) or Wako (www.wako-chem.co.jp), Payzant's claimed purities are thought to be overstated. As noted above, Payzant's Reb A purification method failed when existing commercial quality *Stevia* extracts were used as starting material. The Payzant method of purifying Reb A requires first precipitating out stevioside in a methanol reflux, and Payzant should be so limited as a reference. Putting aside the omission of how 90.2% Reb A purity was obtained, the lack of a reference standard, and the instructions to use anhydrous solvents, the process complexity, low throughput, and low yield in the Payzant method mean that it cannot be used as an industrial process. Moreover, the use of a methanol reflux in isolating Reb A, with concomitant risk of methylated contaminants in the final product, may present a barrier to obtaining "generally recognized as safe" status with government regulators of food products.

The existing art of producing higher purity rebaudioside A uses elaborate sequences of ion exchange columns and other low-throughput procedures. The existing methods used by Kitazume, Payzant, and others do not produce 99+% purity Reb A, whether by crystallization, recrystallization, column purification, or combinations thereof. There are heretofore unsolved problems that have caused unacceptably high levels of contamination in Reb A final products. The existing art in the industrial production of *Stevia* glycosides, including rebaudioside A, typically starts with *Stevia* plant material and produces a *Stevia* extract that has 40% to 90% purity Reb A mixed with various *Stevia* glycosides and "yellow oil"; such extracts are commonly called "*Stevia* extract powder" or "*Stevia* extract", and are herein called "*Stevia* starting material". *Stevia* starting material is abbreviated "SSM" in the Drawings. The lack of an industrial method of producing 99+% purity rebaudioside A has meant that Stevia sweeteners are today typically used (e.g., in pickling) where other flavourants mask the bitter or astringent aftertastes arising from residual contaminants in the *Stevia* sweeteners. Even 1% contamination by other *Stevia* compounds produces a noticeable, bitter aftertaste in Reb A sweeteners, which led Dobberstein, in U.S. Pat. No. 4,612,942, to limit use of *Stevia* glycosides in orally consumable compositions to a level (the "sweetness level threshold") that modified the taste of the compositions, but could not be perceived as sweet. The term "orally consumable composition", as used herein, means substances that are contacted with the mouth of a human or animal, including substances which are taken into and subsequently ejected from the mouth and substances which are drunk, eaten, swallowed or otherwise ingested. There is a need for non-caloric materials that can sweeten, modify, or enhance the flavor of orally consumable compositions such as foodstuffs, smoking compositions, chewing compositions, oral hygiene compositions, and medicinal compositions to improve or vary the sensory perceptions thereof.

In view of the enormous market for a non-caloric, natural sweetener for use in foodstuffs, beverages, medicines, tobacco products, candies, etc., a method of obtaining 99+% purity rebaudioside A has long been sought. 99+% purity Reb A is useful as a reagent, as an ingredient in foods and beverages, as a standalone sweetener, and as a co-sweetener. There is an unmet demand for (1) a method of producing 100% pure, water soluble, rebaudioside A in the lab and (2) a method of producing industrial quantities of 99+% purity, water soluble, rebaudioside A suitable for use as a reagent, as an ingredient in foods and beverages, as a standalone sweetener, and as a co-sweetener. It will be shown that, counter to Payzant's teaching, having a significant water content in the reflux solvent is essential to producing 99+% purity Reb A and to avoiding the contamination reported by all other researchers.

SUMMARY OF THE INVENTION

The primary technical problem to be solved, and the primary object of the invention, is to provide a high throughput, high purity, high yield system and method of isolating and purifying Reb A, with acceptable water solubility for all commercial uses, using commercially available *Stevia* starting material. A second technical problem to be solved by the invention is to maximize yields of 99+% purity Reb A based on the attributes of a given batch of *Stevia* starting material. Solutions to the technical problems must be usable in laboratory-scale volumes as well as in industrial production volumes. Industrial production involves processing hundreds or thousands of kilograms of *Stevia* starting material per batch. Quantitative proof of the inventive step of the invention disclosed herein is that the Reb A final product of the invention has a higher purity than the current primary analytical standard for the highest available purity rebaudioside A (i.e., Chromadex reference standard, Catalog No. ASB-00018226, www.chromadex.com); the Chromadex standard has a certified purity of 98.7%. Reb A of purity greater than the cited Chromadex reference standard is a signature that the invention disclosed herein was likely employed, since no other disclosed method obtains such purities. The higher purity of the Reb A produced by the invention arises from use of the "starting material assay" and the "selected EtOH solvent", as described below. The unmodified word "ethanol" means ethanol denatured with 1% ethyl acetate. The phrase "absolute ethanol" means 100%, non-denatured, anhydrous ethanol. "EtOH" means a solvent consisting of ethanol and water; the percentages of ethanol and water, respectively, are denoted as "xxEt/xxW". For instance, a solvent consisting of 92% ethanol and 8% water would be denoted as "92Et/08W" solvent; a mixture of solids in 92% ethanol and 8% water would be denoted as a "92Et/08W mixture". "Reb A" and "RA" both mean rebaudioside A. The term "RAxx" means a material with a rebaudioside A content of approximately xx percent. For instance, RA80 means a material with a rebaudioside A content of approximately 80%. The term "RAxx.yy" means a material with a rebaudioside A content of xx.yy percent. For instance, RA81.58 means a material with a Rebaudioside A content of 81.58%.

In a laboratory embodiment of the invention, *Stevia* starting material is mixed with a solvent comprising, by volume, between 4% to 15% water and the remaining percentage ethanol, refluxed, and then filtered after a stirred wash. "Water" means potable water, and preferably filtered water compliant with applicable governmental standards for dietary supplement manufacturing. "Solids" means, depending on context, either intermediate product, i.e., retentate obtained by filtering a reflux or wash mixture, or final product. The phrase "100% pure Reb A" is defined in the HPLC Method section of the Examples. Reb A purities of starting materials and final products described herein are determined using the ChromaDex reference standard for Reb A, as described in the HPLC Method section of the Examples. "Producer" means the entity processing *Stevia* starting material to produce purified Reb A. "Higher quality *Stevia* starting material" means *Stevia* starting material with approximately 85% or higher Reb A content. "Lower quality *Stevia* starting material" means *Stevia* starting material with less than approximately 85% Reb A content. One or more reflux stages and stirred wash stages, as defined below, are used to obtain 99+% purity Reb A final product. Using RA90 and higher Reb A purity *Stevia* starting materials, the combination of a single reflux stage and a single stirred wash stage typically produces 99+% purity Reb A. Final product Reb A purities, and Reb A yields, for a given *Stevia* starting material may be targeted and obtained, while minimizing processing costs, by use of the starting material assay with optional mass to solvent ratio assay, as described below. Obtaining a specified final product Reb A purity ("target purity") at minimal processing cost is called "process optimization."

A single reflux in the selected EtOH solvent followed by one or two stirred washes in absolute ethanol typically produces 99+% purity Reb A from higher quality *Stevia* starting material. Such high purities of Reb A have never before been achieved, and the use of a counterintuitive process (Payzant teaches that adding water to the reflux solvent should be avoided) to achieve such purities is a radical departure from the prior art. Rather than eliminate water from the process, a significant, carefully controlled, amount of water, determined using the starting material assay, is essential during a reflux stage.

The number of reflux stages and stirred wash stages required to reach a target purity reflects the level and type of contaminants in a given batch of *Stevia* starting material. In the industrial embodiment of the invention, a reflux stage is much more expensive than a stirred wash stage in terms of time, labor, reagent, heating, and cooling costs. The industrial process for a given batch of *Stevia* starting material typically balances target purity, yield, and cost of production.

In the invention, typical reflux stages use 1 gram of *Stevia* starting material for every 4 ml of the selected EtOH solvent. Generally speaking, the lower the Reb A content of the *Stevia* starting material, (i) the higher the water content (within the 4% to 15% range) needed in the reflux solvent to produce 99+% purity Reb A and (ii) the greater the probability that more than one reflux stage will be needed to produce 99+% purity Reb A final product. The higher the water content in the reflux solvent, and the more reflux stages used, however, the lower the yield of Reb A. In contrast to a reflux stage, a stirred wash stage preferably uses absolute ethanol as a solvent. Denatured ethanol or other alkanols can be used as a solvent in the stirred wash stage; using denatured ethanol or absolute ethanol in the stirred wash stage avoids food safety issues associated with other alkanols.

In one laboratory embodiment of the invention, an RA89.95 *Stevia* starting material (*Stevia* starting material that is approximately 90% Reb A by weight is called herein, "RA90 starting material"; similarly, *Stevia* starting material that is approximately 80% Reb A by weight is called herein, "RA80 starting material"; similarly, *Stevia* starting material that is approximately 70% Reb A by weight is called herein, "RA70 starting material"; etc) is dissolved in 94% ethanol, 6% water at a ratio of 1 gram of RA90 starting material to 4 mls of the selected EtOH solvent. The selected EtOH solvent is also called the "reflux solvent". A mixture of *Stevia* starting material and reflux solvent is called the "reflux mixture". "Starting material" means *Stevia* starting material, in the case of an initial reflux, and retentate obtained by filtering a refluxed mixture or a stirred wash, in the case of stages after an initial reflux stage. The mixture of RA90 starting material and reflux solvent is heated with vigorous stirring in a reflux apparatus, equipped with a condenser, from room temperature to approximately 79° C. to 80° C. (the boiling point of absolute ethanol is 79° C.; the boiling point of the reflux mixture is usually not more than 80° C.). As the reflux mixture temperature is increased to and maintained between 79° C. to 80° C., at one atmosphere of pressure, the mixture becomes opalescent and viscous as crystals of rebaudioside A begin to precipitate. The mixture is typically refluxed for one hour, then filtered (paper or glass fiber filter media, e.g., Whatman GF/A filter paper (Whatman, Florham Park, N.J.), in a laboratory embodiment) and the wet solids placed in 100% absolute ethanol at a ratio of 1 gram of wet solids to 4 mls of wash solvent, typically absolute ethanol, to create a "wash mixture". The wash mixture is stirred for 15 minutes at room temperature. After stirring, the wash mixture is filtered over filter paper and the retentate solids dried in an oven at 80° C. The dried solids are 100% Reb A and represent a recovery of approximately 81% of Reb A in the starting material. The final product has an approximate solubility in water of 33% (1 gram in 3 mls final volume), which is adequate for all commercial uses.

The apparatus used in the industrial embodiment of the invention typically comprises one or more jacketed, stainless steel pressure vessels ("tanks" or "mixing tanks"), each typically of multiple thousand liter capacity, equipped for mixing (e.g., equipped with flexible scraper blades), heating (steam in jacket), and cooling (chilled water in jacket), and equipped with inlet and outlet paths and a reflux condenser. Additional equipment includes one or more centrifugal decanters (typically continuous flow models), pumps, valves, holding tanks, pipes that interconnect the mixing tank(s), decanter(s), and other elements of the apparatus, and preferably a process control system. The industrial process of the invention uses the same parameters as the lab process, except centrifugal decanters are used instead of filter paper, the mass and volume of starting material and solvent, respectively, is much greater (limited primarily by tank volume), chilled water cooling after reflux is typically used, and after the final reflux or stirred wash stage, an "ethanol purge and drying" stage is used in which the decanter retentate is dissolved and stirred in 80° C. water to evaporate residual ethanol before spray drying. The final product of the industrial process is typically 99+% purity Reb A with approximately 33% solubility in water. This level of Reb A purity is a breakthrough in *Stevia* processing, especially in industrial quantities.

Using more than one reflux stage and stirred wash stage, as defined below, lower quality *Stevia* starting material can be processed using the invention to produce a final product of 99+% purity Reb A. Using lower quality *Stevia* starting materials reduces yields and requires more refluxes to obtain 99+% Reb A purity final product.

DETAILED DESCRIPTION OF THE PREFERRED EMBODIMENTS

Figure 1:
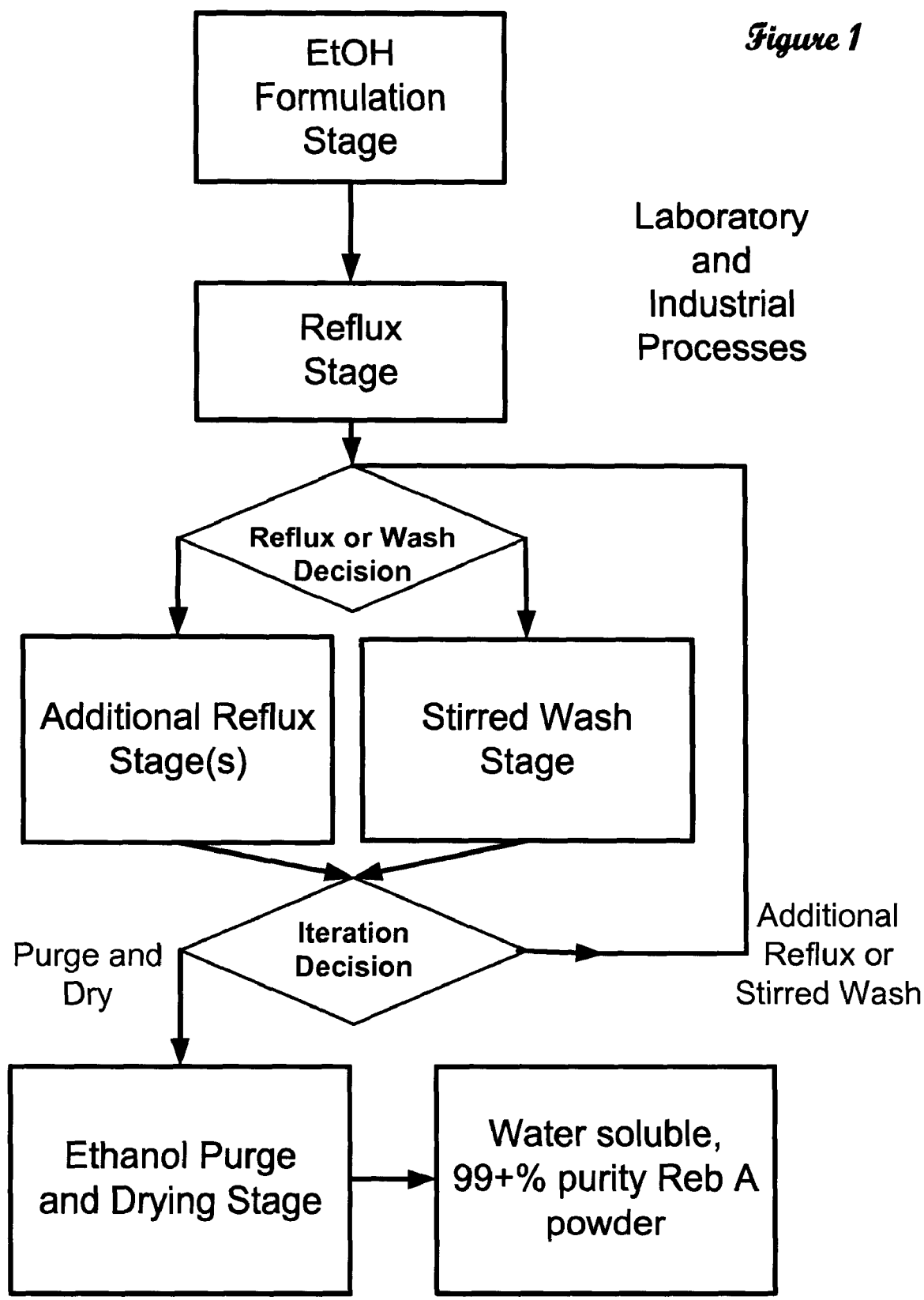
FIG. 1 shows an overall view of the laboratory embodiment of the invention.

The invention comprises (i) a high purity, high yield laboratory process that provides 100% pure rebaudioside A using *Stevia* starting material; (ii) a high throughput, high purity, high yield industrial process, derived directly from the laboratory process, that provides commercial quantities of 99+% purity rebaudioside A using *Stevia* starting material; (iii) the rebaudioside A made by those processes; (iv) uses of such rebaudioside A; and (v) a means of maximizing yields of a target purity of Reb A based on the attributes of a given lot of *Stevia* starting material.

The utility of the laboratory process lies in the ability to produce 100% pure, water soluble Reb A for research, analytic, and synthetic purposes. The utility of the industrial process lies in the ability to produce commercial quantities (e.g., thousands of kilograms) of 99+% purity Reb A for the beverage, food, baking, candy, personal care product, pharmaceutical, tobacco, and other industries, as well as for research, analytics, and synthesis. As a result of the perceived sweetness of very low concentrations of pure Reb A, for most uses, including beverages, Reb A water solubility of less than 1% is acceptable (concentrates require higher solubility, but within the final product solubility range provided by the invention).

Reb A is significantly less expensive to produce using the invention compared with existing processes, even though the invention produces Reb A of far higher purity. The means provided herein of maximizing yields of 99+% purity Reb A based on the attributes of a given lot of *Stevia* starting material enables even greater savings in production costs compared with existing processes. *Stevia* starting material with greater than 40% purity Reb A content is preferred for use with the invention; the additional reflux stages typically required for *Stevia* starting material of less than RA40 quality typically make the process financially disfavored, and *Stevia* starting materials with greater than 40% purity Reb A are readily available. RA40 and higher *Stevia* starting materials are available from Shandong Chengwu Aoxing *Stevia* Production Co., Ltd., Datianji Town, Chengwu County, Shandong, People's Republic of China, as well as other sources known in the art. *Stevia* starting materials typically do not exceed RA80; however, a few commercially available, significantly more expensive *Stevia* extracts, such as the one sold under the product name of Rebaudio by Morita Kagaku Kogyou, Ltd., Joto-ku, Osaka, Japan, have approximately 90% Reb A content. In the reflux and stirred wash stages of the present invention, denatured ethanol is typically preferred for cost reasons, particularly for the industrial embodiment of the invention; absolute ethanol is approximately ten times as expensive as denatured ethanol in the U.S., but in locales where both denatured and absolute ethanol have substantially the same cost, absolute ethanol is preferred over denatured ethanol for use as a sole solvent and as a reflux solvent component. Denatured ethanol containing additives other than 1% ethyl acetate (e.g., ethanol denatured with 5% isopropanol) can be used in the invention, but typically result in reduced yields and purity of final product. Alkanols other than ethanol can be used, but using ethanol avoids food safety issues related to other alkanols.

FIG. 1 shows an overview of the invention. A basic embodiment used with higher quality *Stevia* starting materials comprises three or four stages: an EtOH formulation stage, a reflux stage, optional stirred wash stage (typically required to produce 99+% purity Reb A), and an ethanol purge and drying stage. In embodiments that use lower quality *Stevia* starting material, a second reflux stage is typically added before a stirred wash stage to maximize purity of the Reb A final product. The decision points of whether to follow the first reflux with a single stirred wash stage or with more reflux stages (with or without intermediate and final stirred wash stages) are shown in FIG. 1 (and certain other Figures) and labelled as "Iteration Decision". An EtOH formulation stage always includes a starting material assay and may include a mass to solvent ratio assay. The term "starting material assay" includes assays of wet solids retentate following a reflux stage or a stirred wash stage; *Stevia* starting material is the starting material for a first reflux stage; wet solids retentate is the starting material for a stage subsequent to the first reflux stage. Starting material assay is abbreviated "SMA" in the Drawings.

Figure 6:
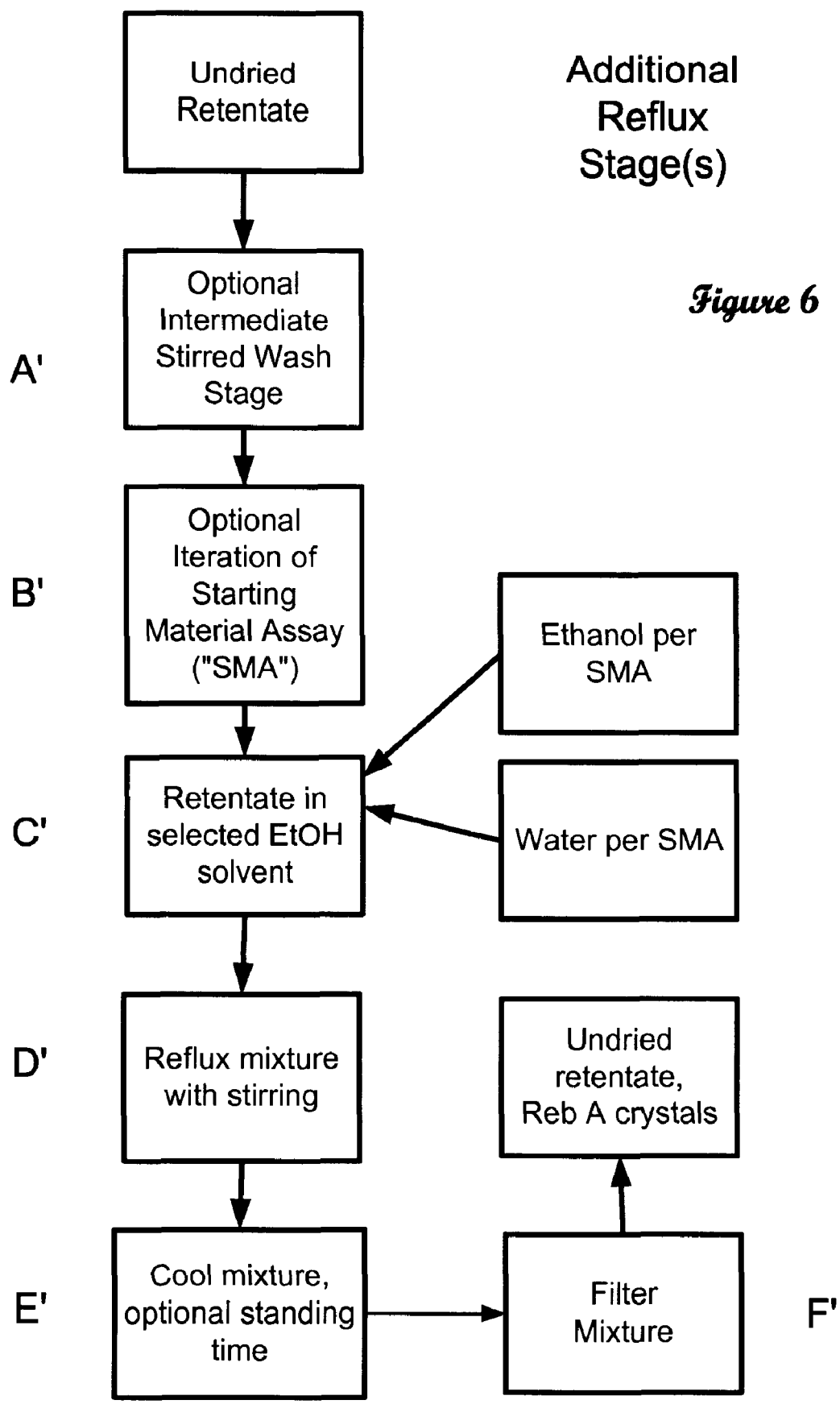
FIG. 6 shows the steps in additional reflux stages.

Since there is an inverse relationship between yield and purity of the Reb A final product, determining the most cost efficient method to produce a target Reb A purity, e.g., 99+% purity Reb A, from a given *Stevia* starting material is important in process optimization and the economics of production. Process optimization is performed by first using the laboratory embodiment, and when the process is optimized at laboratory scale, the results of optimization are applied at industrial scale. The preferred embodiment of process optimization comprises using at least one starting material assay, producing final product Reb A purity equal to or greater than the target purity, and progressively replacing any additional reflux stage(s) (an "additional reflux stage" is one other than the first reflux stage, as described in more detail below and as shown in FIG. 6) with (i) one or more stirred wash stages, (ii) use of a different mass to solvent ratio in the remaining reflux stage(s) and/or stirred wash stage(s), or (iii) a combination of (i) and (ii). A decision point of whether to perform an additional reflux or a stirred wash, or whether to proceed to the ethanol purge and drying stage, are denoted as "Iteration Decision" in the Drawings. For instance, when processing a given higher quality *Stevia* starting material for the first time, if a single reflux (typically, mass to volume ratio of 1 to 4) stage and one stirred wash stage does not produce 99+% purity Reb A in the laboratory embodiment of the invention, a mass to volume ratio assay of the first reflux stage solvent, and optionally of the first stirred wash stage solvent, is typically introduced into the EtOH formulation stage(s) in an effort to obtain the target purity without a second stirred wash stage or a second reflux stage. The processing cost of a stirred wash stage is much less than the cost of a reflux stage, and the processing cost of a single stirred wash stage is less than that of two stirred wash stages.

If the Reb A purity of the final product is above the target purity and if replacing the final additional reflux stage with a stirred wash stage does not produce the target purity, a higher mass to solvent ratio in the former penultimate (and earlier) reflux stage(s) may achieve the target purity and avoid the need for the final additional reflux stage. A higher mass to solvent ratio is typically used in this circumstance if the cost of using and recovering the additional ethanol in the reflux stage(s) is less than the cost of heating and cooling in an additional reflux stage using the original mass to solvent ratio, so long as the target purity is obtained.

If, after replacing a final additional reflux stage with a stirred wash and/or different mass to solvent ratio in the reflux stage(s), the Reb A purity of the final product is still above the target purity, the producer may elect to further reduce processing costs by substituting a stirred wash stage for a reflux stage, and/or by using a different mass to solvent ratio in the remaining reflux stage(s) or stirred wash stage(s). If, after replacing a final reflux stage with a stirred wash or using a different mass to solvent ratio, the Reb A purity of the final product is below the target purity previously achieved using the additional reflux stage at issue, the producer reverts to using the deleted additional reflux stage, since the target purity cannot be achieved without that reflux stage. In this way, guided by EtOH formulation, different permutations of reflux, and stirred wash stages, the cost of producing a given target purity using a given *Stevia* starting material is minimized. Process optimization is typically performed using the laboratory embodiment of the invention; the optimal process for a given *Stevia* starting material is then applied at industrial scale. With lower quality *Stevia* starting material, it is unlikely that processing using a single reflux and single stirred wash will produce a 99+% purity Reb A final product. Processing lower quality *Stevia* starting materials that contain "stubborn" contaminants may require at least two EtOH reflux stages and an absolute ethanol reflux stage, instead of two EtOH reflux stages and a stirred wash stage, as Example 1 shows (Example 1 used a blend of *Stevia* starting material that contained RA40).

Figure 2:
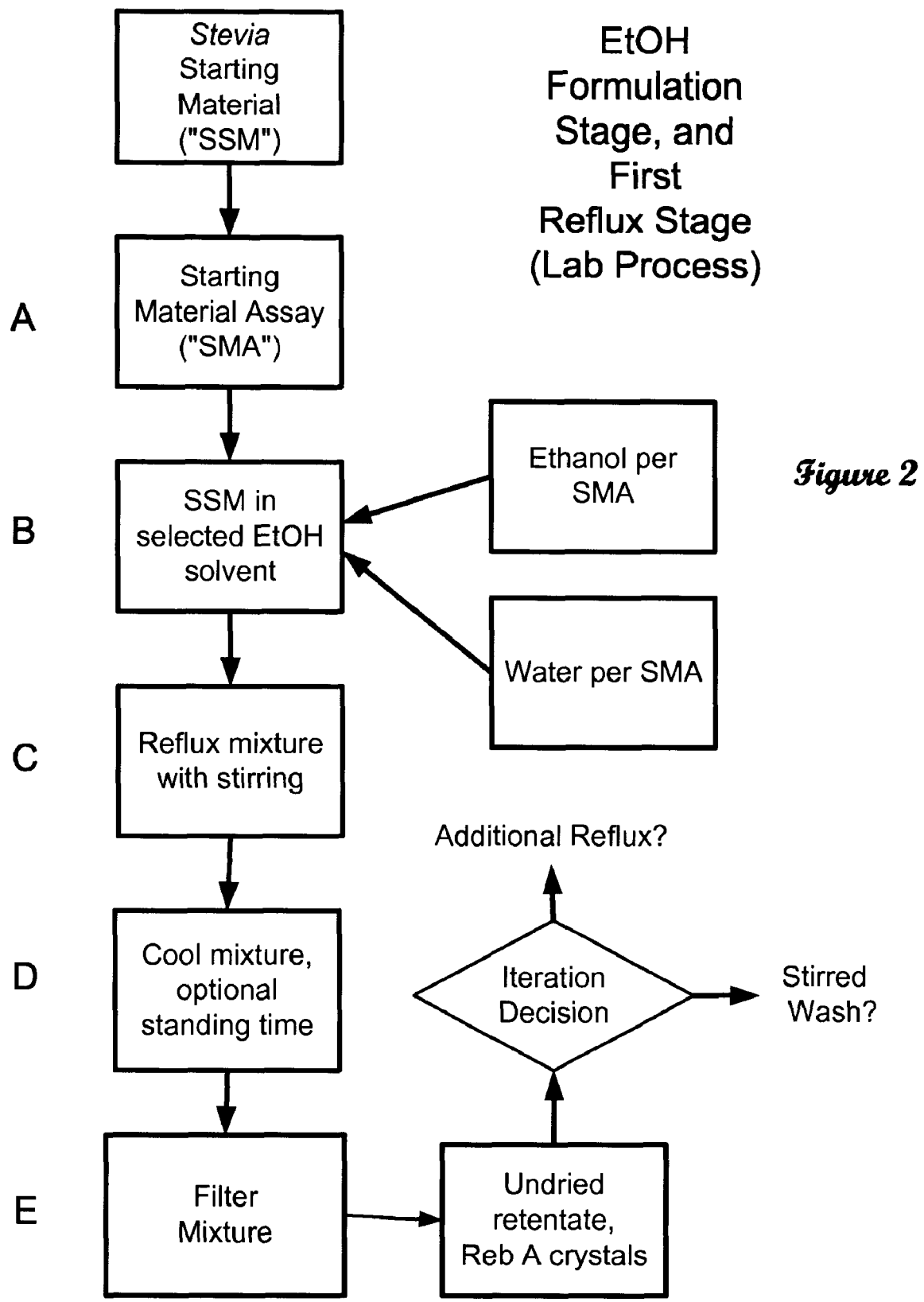
FIG. 2 shows the steps in the reflux stage of the laboratory process.

As shown in FIG. 2, step A comprises the EtOH formulation stage, steps B to E comprise the reflux stage of the laboratory embodiment of the invention. Mixing and refluxing the *Stevia* starting material in the selected EtOH solvent formulated for a given *Stevia* starting material and then isolating rebaudioside A by filtering the refluxed mixture is a "reflux stage". An additional reflux stage comprises mixing and refluxing retentate (the solids isolated by filtering the mixture from the immediately previous stage) in the selected EtOH solvent formulated for a given *Stevia* starting material or retentate and then isolating rebaudioside A by filtering the refluxed mixture.

Figure 3:
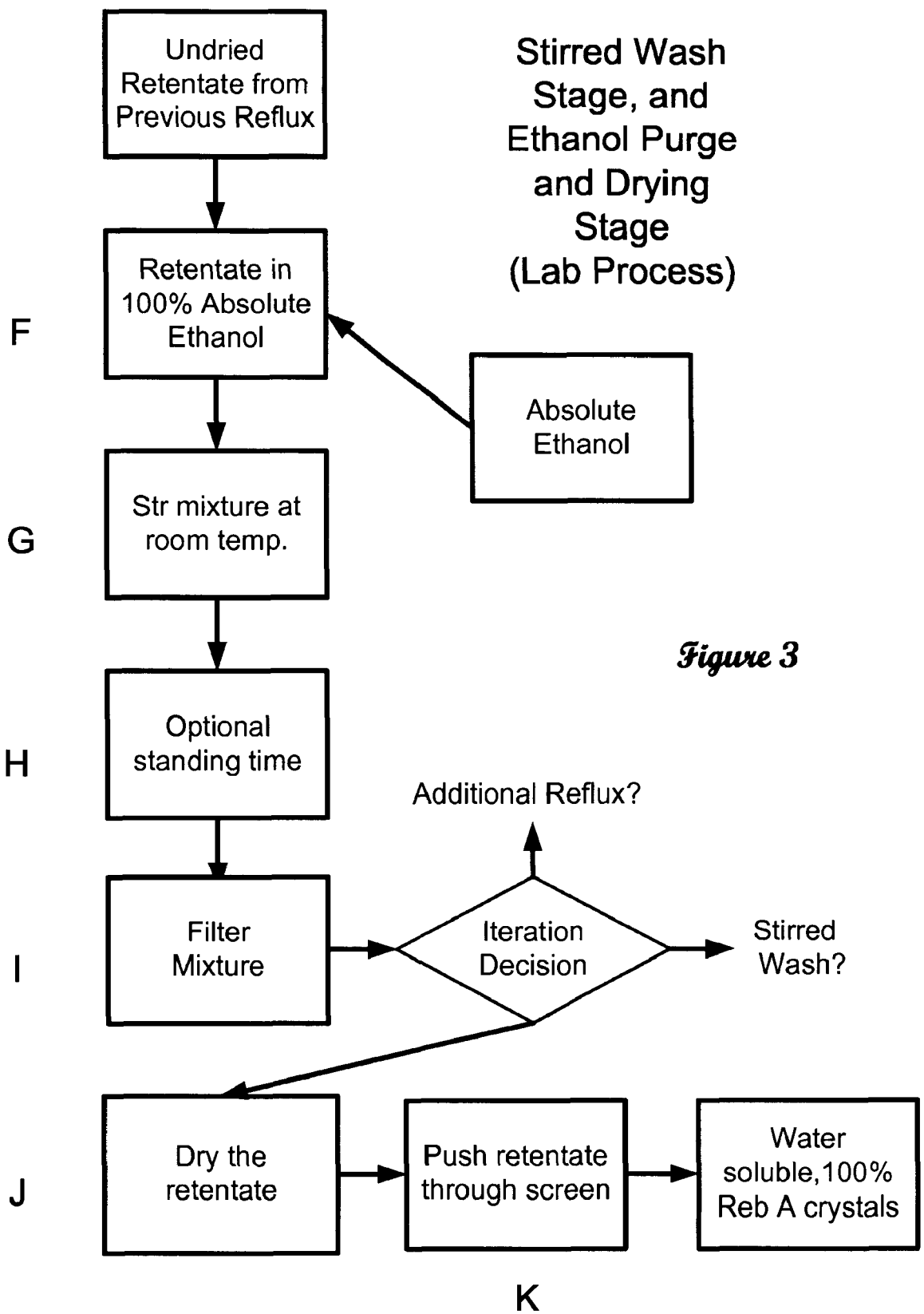
FIG. 3 shows the steps in the stirred wash stage of the laboratory process.

As shown in FIG. 3, steps F to I comprise the stirred wash stage of the laboratory embodiment of the invention. Mixing and stirring the isolated rebaudioside A in a denatured or absolute ethanol wash and then isolating rebaudioside A by filtering the wash mixture is a "stirred wash stage". As discussed above, absolute ethanol is preferred as the solvent in a stirred wash, but cost management may dictate using denatured ethanol in the stirred wash stage. Steps J to K comprise the ethanol purge and drying stage of the laboratory embodiment of the invention. In the laboratory embodiment, steps J to K, the ethanol purge and drying stage, are also known as "purging the ethanol and drying the isolated retentate."

As shown in FIG. 2, in an embodiment of the invention for laboratory use, *Stevia* starting material is mixed with a solvent comprising ethanol and water (between 4% to 15%, by volume, of water). Step A in the laboratory embodiment is a determination of the water to ethanol balance in the solvent to be used in the reflux solvent. The preferred means of determination of the water to ethanol balance is an assay of the *Stevia* starting material, as described below ("starting material assay"). An alternative means of determination of the water to ethanol balance is to use a guideline, called herein the "reflux solvent approximation," i.e., for every 5% decrease in Reb A purity below 90% Reb A purity in the *Stevia* starting material, based on the asserted or labeled purity of a batch of *Stevia* starting material, the water content of the reflux solvent should be increased 1% above a baseline of 6% water; the remaining volume of the reflux solvent is ethanol. For example, the reflux solvent approximation teaches using a reflux solvent of 8% water, 92% water, volume to volume, to process RA80 starting material and ultimately produce 100% pure Reb A (obtaining such purity typically requires at least two reflux stages when using RA80 *Stevia* starting material). The reflux solvent approximation was derived by the first-named inventor from empirical data collected in perfecting the starting material assay.

Figure 4:
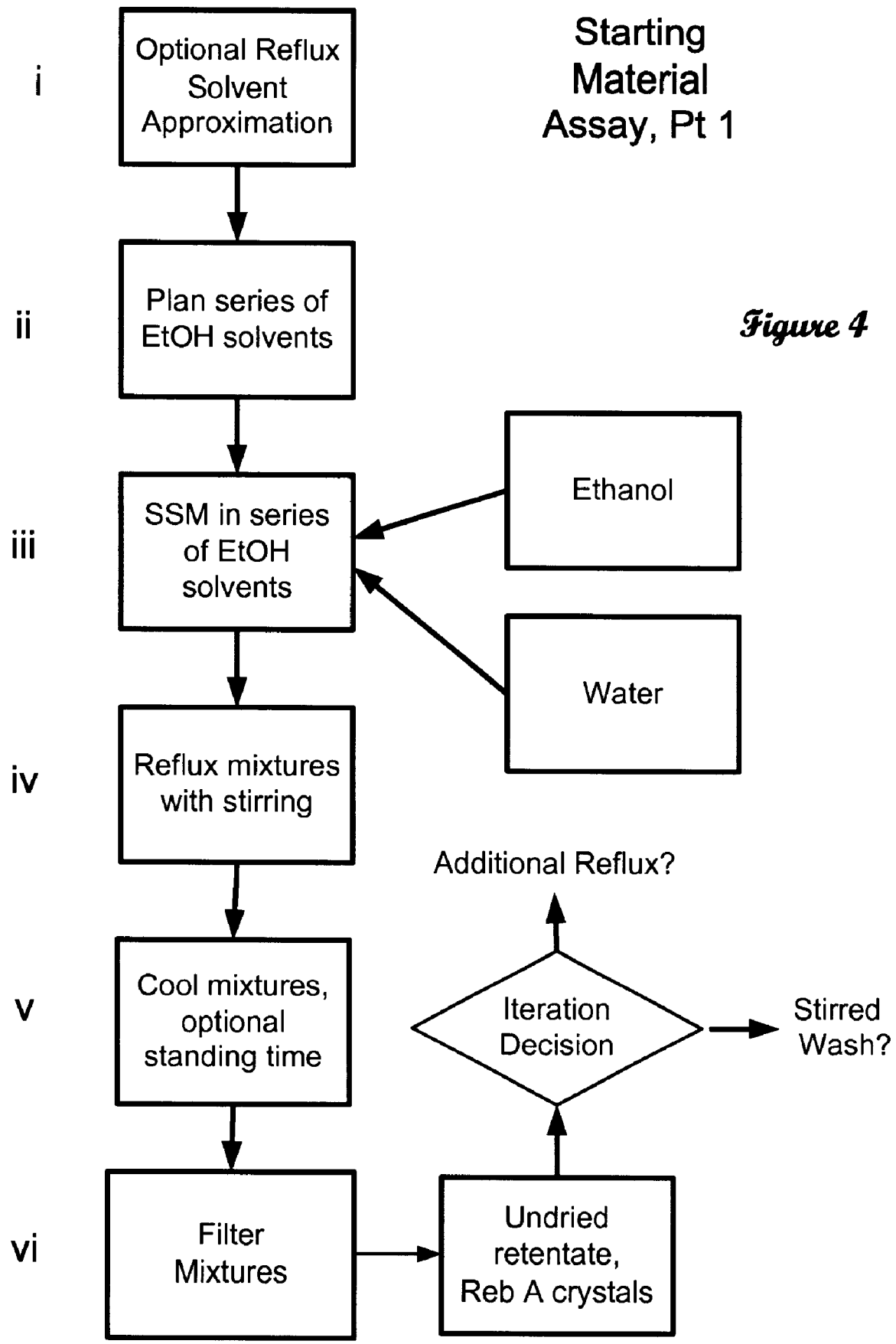
FIG. 4 shows the first half of the starting material assay.
Figure 5:
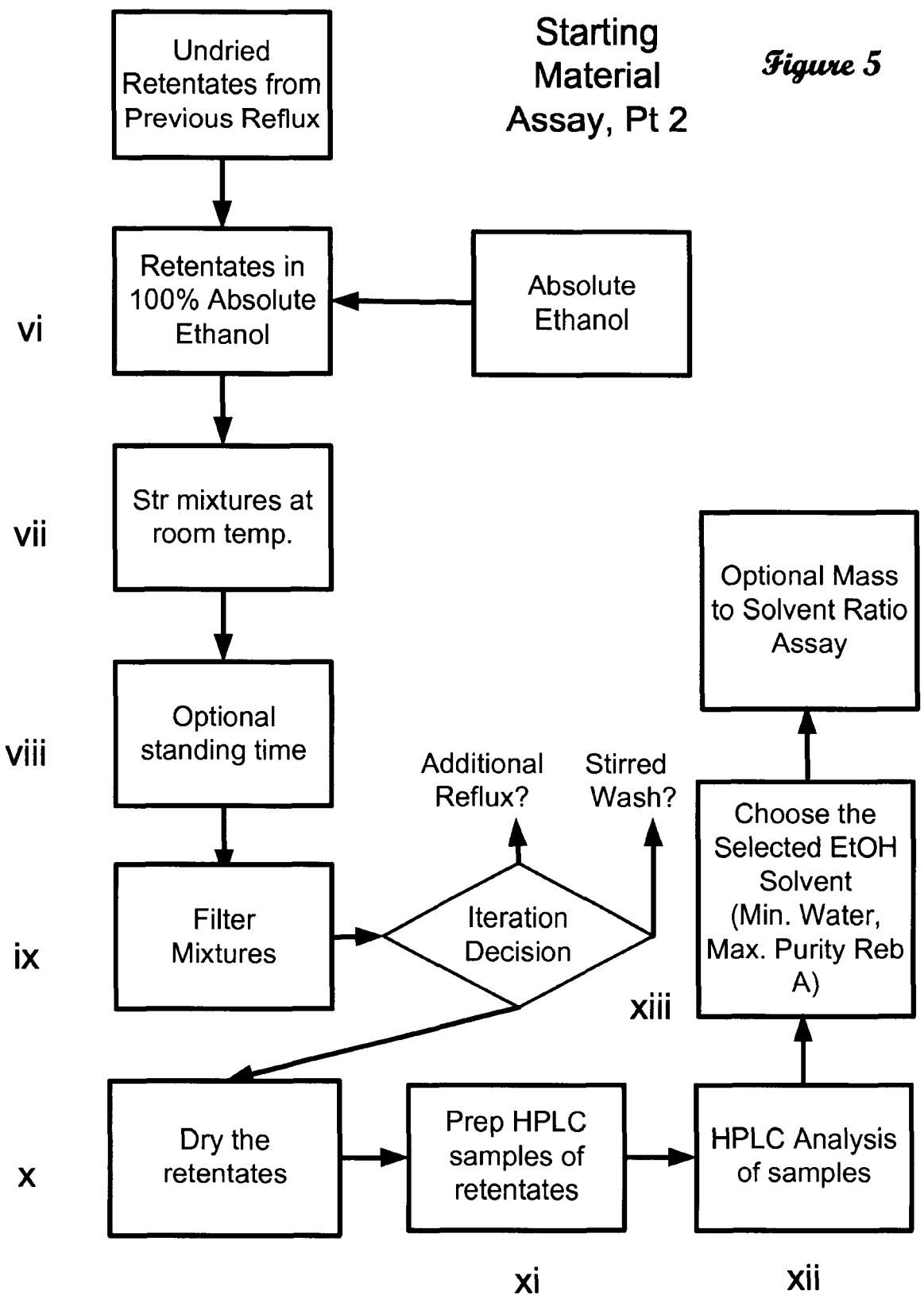
FIG. 5 shows the second half of the starting material assay.

The starting material assay is the preferred means of determination of the water to ethanol balance in the reflux solvent since the starting material assay reveals the minimum, not just an approximation of, water content needed in the reflux solvent to produce (in conjunction with one or more stirred wash stages) a target purity, e.g., 99+% purity Reb A. Water content in excess of the minimum significantly decreases yields of Reb A final product. As shown in FIGS. 4 and 5, the starting material assay is conducted by using a coordinated set of solvents in which the water content is uniformly incremented 0.5% to 15%, or within a subset of that range, e.g., 2% to 10%; the balance of each solvent is ethanol (each combination of water and ethanol is called herein a "test solvent"). The asserted or labeled purity of the *Stevia* starting material is an input in the assay only to the degree that the asserted or labeled Reb A purity and the reflux solvent approximation can be used to center the initial set of test solvents. For instance, a starting material assay for *Stevia* starting material labeled as RA80 would typically use a set of test solvents centered around 8% water and 92% ethanol. In the starting material assay, a sample of *Stevia* starting material taken from a given batch or lot of *Stevia* starting material ("sampled batch") is mixed with each in a series of test solvents (e.g., 2% water and 98% ethanol, 4% water and 96% ethanol, 6% water and 94% ethanol, etc.) in a mass to volume ratio of 1 g *Stevia* starting material to 4 ml of test solvent.

As explained in more detail below, the ratio of *Stevia* starting material to reflux solvent can be varied over a range of from 2 to 10 or more parts by volume of EtOH solvent per 1 part of *Stevia* starting material by mass, but is preferably from 3 to 6 parts by volume of EtOH solvent per 1 part of *Stevia* starting material by mass, and is most preferably approximately 4 parts by volume of the EtOH solvent per 1 part of *Stevia* starting material by mass. As shown in the Example 7, a 1:4 ratio of *Stevia* starting material to selected EtOH solvent generally maximizes yield of Reb A in a single reflux, single stirred wash process using higher quality *Stevia* starting material. Each mixture of the *Stevia* starting material and test solvent (each, a "test mixture") is heated (typical heating rate of 4° C./min.) with vigorous stirring in a reflux apparatus, equipped with a condenser, from room temperature to approximately 79° C. to 80° C. at one atmosphere of pressure, refluxed for approximately one hour, then cooled for approximately one hour (typically, flasks are placed in an ice bath) and filtered over filter paper. The wet solids, or retentate, from each test mixture are each placed in 100% absolute ethanol at a ratio of 1 gram of wet solids retentate to approximately 4 mls of solvent (each, a "test wash mixture").

If a ratio of *Stevia* starting material to EtOH solvent other than 1:4 was used in the reflux, the same ratio of wet solids retentate from each test mixture to 100% absolute ethanol can be used for the test wash mixture. Typically, however, a 1:4 ratio of *Stevia* starting material to ethanol in the test wash mixture is used since higher ratios typically have minimal effect on ultimate Reb A purity and may decrease Reb A yields.

Each test wash mixture is stirred for 15 minutes at room temperature. After stirring, each test wash mixture is filtered over filter paper and the retentate solids from filtering are dried in an oven, preferably a blower oven, at or minimally above 79° C. to produce dried samples (each, a "test sample"). Oven temperature should not be too much above 80° C. to avoid degrading the test sample or igniting the residual ethanol. Each test sample is tested for Reb A purity using the HPLC analysis method described in the HPLC Method section of the Examples below. For a target purity of 100% pure Reb A final product, the test solvent (i) corresponding to the test sample indicated as 100% pure Reb A (or highest Reb A purity in the event a single reflux, single stirred wash fails to produce 100% pure Reb A) in the HPLC analysis and (ii) containing the lowest water content is selected ("first iteration result") as the solvent for processing the remainder of the sampled batch. For instance, if test solvents containing 6%, 8%, and 10% water (the balance of each test solvent is ethanol) each produces a test sample of 100% pure Reb A, then a 6% water, 94% ethanol solvent is the first iteration result and (unless a second iteration of the starting materials assay is used to refine the result) would be used to process the remainder of the sampled batch.

The starting material assay may be multiply iterated to select a solvent that further optimizes the yield of 100% pure Reb A. In a second iteration of the starting material assay, the water content in the coordinated set of test solvents is uniformly decremented below the water content of the first iteration result, but in smaller increments, e.g., decrements of 0.5% water. For example, if the first iteration result were 6% water, 94% ethanol, the test solvents in the second iteration could be 6.0%, 5.5%, 5.0%, and 4.5% water. The remainder of the process as described above (first reflux, stirred wash, drying, and HPLC analysis) is performed using second iteration test solvents, test mixtures, and test wash mixtures. The second iteration test solvent (i) corresponding to the test sample indicated as 100% pure Reb A (or highest Reb A purity in the event a single reflux, single stirred wash fails to produce 100% pure Reb A) in the HPLC analysis and (ii) containing the lowest water content is selected as the solvent for processing the remainder of the sampled batch and replaces the first iteration result. For instance, if test solvents containing 6.0%, 5.5%, and 5.0% water (the balance of each test solvent is ethanol) each produces a test sample of 100% pure Reb A, then a 5% water, 95% ethanol solvent would be used to process the remainder of the sampled batch. More than two iterations of the starting material assay can be performed to more finely optimize the selection of reflux solvent, e.g., a third iteration could use 0.1% decrements of water content below the second iteration result.

The water and ethanol solvent selected using the reflux solvent approximation or the starting material assay is called the "selected EtOH solvent." "EtOH" is a trivial name for a blend of ethanol and water. For convenience, the *Stevia* starting material to be processed using the selected EtOH solvent (even if selected using the reflux solvent approximation) is called the "sampled batch". The starting material assay typically produces a much more accurate result than the reflux solvent approximation, and is the preferred method of determining the selected EtOH solvent.

Using the starting material assay or the reflux solvent approximation, including multiple iterations thereof, is called "formulating a selected EtOH solvent for the starting material" and is also called the "EtOH formulation stage". By substituting the wet solids retentate obtained by filtering a reflux mixture (or a stirred wash mixture) in place of *Stevia* starting material in the starting material assay, an EtOH formulation stage can be performed before an additional reflux stage (or stirred wash stage). Performing an EtOH formulation stage before each reflux is usually done only if very large quantities of wet solids retentate are being processed or if yields and purity of a previous reflux stage did not meet expectations.

An EtOH formulation stage can optionally include, after determining the selected EtOH solvent, varying the ratio of EtOH solvent to *Stevia* starting material (before an initial reflux stage) or varying the ratio of EtOH solvent to wet solids retentate (before an additional reflux stage or a stirred wash stage) to determine the ratio that maximizes Reb A yield. This assay is called the "optional mass to volume ratio assay." The ratio of the mass of *Stevia* starting material or wet solids retentate to the volume of the selected EtOH solvent can be varied over an open-ended range starting from at least 3 parts by volume of the selected EtOH solvent per 1 part of starting material by mass, but is preferably from 3 to 10 parts by volume of the selected EtOH solvent per 1 part of starting material by mass, more preferably from 4 to 6 parts by volume of the selected EtOH solvent per 1 part of starting material by mass, and is most preferably approximately 4 parts by volume of the selected EtOH solvent per 1 part of starting material by mass. Using higher quality *Stevia* starting material, maximum Reb A yield is typically obtained at, or very close to, a ratio of 4 parts by volume of the selected EtOH solvent per 1 part of *Stevia* starting material (before an initial reflux stage), or of wet solids retentate (before additional reflux stages) by mass. If very large quantities of wet solids retentate are being processed, or if yields and purity of a previous reflux stage did not meet expectations, the EtOH formulation stage and optional mass to volume ratio assay can be repeated before an additional reflux. For processing higher quality *Stevia* starting materials, the first optional mass to volume ratio assay is usually performed using small increments of ratios near 1:4 to determine the mass to solvent ratio that produces maximum Reb A yield. For instance, ratios of 1:3.8, 1:3.9, 1:4.0, 1:4.1, and 1:4.2 (m/v) may be used in a first optional mass to volume ratio assay when processing higher quality *Stevia* starting materials.

Higher ratios of *Stevia* starting material to EtOH solvent in the reflux, such as 1:6 or 1:8 (m/v), are sometimes needed to process lower quality *Stevia* starting material (e.g., RA40 to RA85) when the target purity is 99+% purity or 100% pure Reb A. As shown in the Example 7, Reb A yields typically decrease as higher ratios of *Stevia* starting material to the selected EtOH solvent in a reflux, and of wet solids retentate to ethanol in a stirred wash or in a second or subsequent reflux, are used; costs also increase as higher ratios are used, since more reagents and bigger tanks are used. As shown in Example 7, such higher ratios may be necessary to produce 100% pure Reb A final product from lower quality *Stevia* starting materials using two reflux stages. Ratios of *Stevia* starting material to the selected EtOH solvent in a first reflux stage, or of wet solids retentate to the selected EtOH solvent in an additional reflux stage, below 1:3.5 (m/v) typically produce very viscous mixtures that are difficult to process, produce lower yield of Reb A, and produce lower purity Reb A. Ratios of *Stevia* starting material to the selected EtOH solvent in a first reflux stage, or of wet solids retentate to the selected EtOH solvent in a subsequent reflux stage, below 1:3 (m/v) may produce mixtures that crust or solidify when cooled, which greatly complicates processing.

As a general rule, a mass to volume ratio of *Stevia* starting material to the selected EtOH solvent in a first reflux stage, or of wet solids retentate to the selected EtOH solvent in an additional reflux stage, of 1:4 or very close thereto is the most preferred ratio, especially for higher quality *Stevia* starting material, since the maximum Reb A yield will be at or very close to a 1:4 (m/v) ratio.

Figure 11:
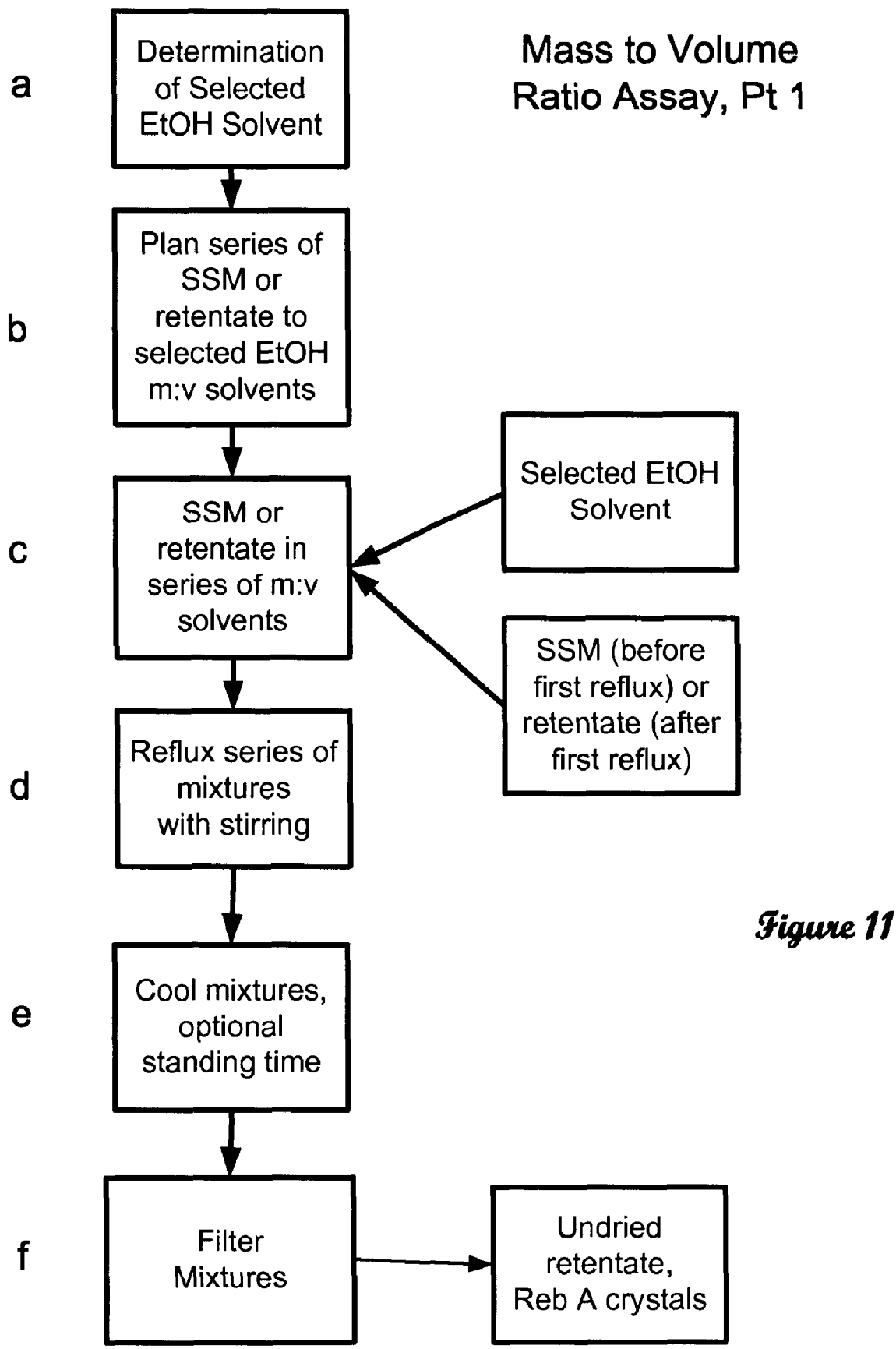
FIG. 11 shows the first half of the mass to volume ratio assay.
Figure 12:
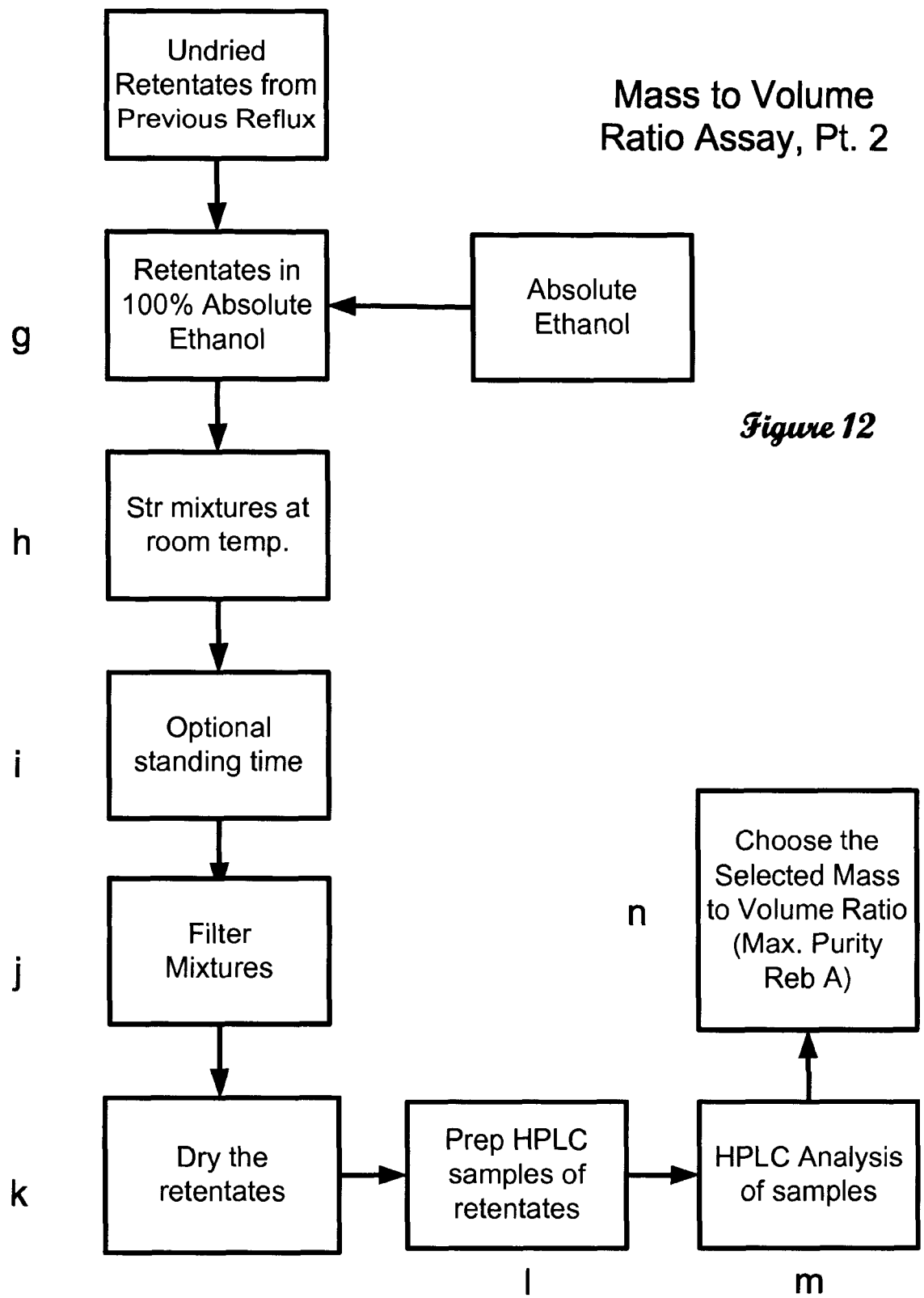
FIG. 12 shows the second half of the mass to volume ratio assay.

As shown in FIGS. 11 and 12, the steps used in a mass to solvent ratio assay are very similar to those in the starting materials assay, except that, for a given mass of *Stevia* starting material (or following a first reflux, the mass of wet solids retentate), in a mass to solvent ratio assay, for a given mass of *Stevia* starting material (or following a first reflux, the mass of wet solids retentate), the volume of the selected EtOH solvent is varied and the mass to volume ratio that maximizes Reb A purity of the final product is typically chosen for processing the sampled batch. The mass to volume ratio assay is optional and is typically only used with lower quality *Stevia* starting material; as shown in Example 7, a higher mass to volume ratio (e.g., 1:6) of starting material to selected EtOH solvent in a reflux can sometimes produce 100% pure Reb A with fewer refluxes. The mass to volume ratio assay can be reiterated (using smaller increments and decrements of selected EtOH solvent volume) to optimize the accuracy of the mass to volume ratio for a given *Stevia* starting material or retentate.

As the data in Example 1 shows, 1% more water in the reflux solvent above optimum water content can reduce the yield of 100% pure Reb A by 1% or more. The fine tuning of optimum water content is very important in the economics of the industrial process. The asserted or labeled Reb A content of *Stevia* starting materials may differ substantially from actual Reb A content, and a given batch of *Stevia* starting material often is a blend of *Stevia* extract from many sources. The selected EtOH solvent determined by the starting material assay is specific to a given batch of *Stevia* starting material. One of the primary uses of the laboratory embodiment of the invention is to perform the starting material assay for the industrial embodiment of the invention.

As shown in FIG. 2, after the EtOH solvent is selected, in a laboratory embodiment of the invention, a producer-determined amount of the sampled batch is processed using the reflux and stirred wash stages, as follows. *Stevia* starting material of the sampled batch is mixed with the selected EtOH solvent in a mass to volume ratio of 1 g *Stevia* starting material to 4 ml of selected EtOH solvent (or other ratio determined using the EtOH formulation stage, including any optional mass to volume ratio assay). The mixture of the *Stevia* starting material and the selected EtOH solvent ("reflux mixture") is heated (typically, 4° C./min.) with vigorous stirring in a reflux apparatus, equipped with a condenser, from room temperature to approximately 79° C. to 80° C. at one atmosphere of pressure, and maintained in reflux typically for one hour; the reflux mixture is then cooled for one hour (typical cooling rate of −1.8° C./min., e.g., by placing flasks in an ice bath) and then filtered over filter paper. Allowing the solvent mixture to stand after completion of reflux and before filtering marginally increases Reb A yield when processing higher quality *Stevia* starting material, but significantly increases Reb A yield when processing lower quality *Stevia* starting material.

As shown in FIG. 3, the wet solids retentate from the first reflux stage are placed in 100% absolute ethanol at a ratio of 1 gram of wet solids to 4 mls of solvent ("wash mixture") (or other ratio determined using the EtOH formulation stage, including any optional mass to volume ratio assay). The wash mixture is stirred for 15 minutes at room temperature. Ratios of wet solids retentate to ethanol below 1:3.5 (m/v) in a stirred wash stage may produce mixture viscosity that impairs processing. Using higher quality *Stevia* starting materials, ratios of wet solids retentate to ethanol above 1:4 (m/v) in a stirred wash stage produce negligible improvement in Reb A purity and typically decrease Reb A yield. Therefore, a mass to volume ratio of wet solids retentate to ethanol in a stirred wash stage of 1:4 or very close thereto is the most preferred ratio when using higher quality *Stevia* starting materials. After stirring, the wash mixture is filtered over filter paper and the retentate solids from filtering are dried in an oven, preferably a blower oven at or minimally above 79° C. for up to two hours to produce dried solids. An oven temperature of 80° C. safely vaporizes the ethanol in the wash mixture without igniting the ethanol, and thus purges the retentate solids of ethanol. Allowing the wash mixture to stand after completion of stirred wash and before filtering marginally increases yields when processing higher quality *Stevia* starting material, but significantly increases yields when processing lower quality *Stevia* starting material. If a powdered final product is desired, the dried solids are pushed through a 30-mesh screen, resulting in a final product of coarse white powder (Reb A final product).

The final product, dried solids, produced using higher quality *Stevia* starting material and a single reflux, single stirred wash process is typically 100% Reb A and typically represents a recovery of approximately 81% of Reb A in the starting material. The final product has solubility in water of 33% (1 gram in 3 mls final volume), which is adequate for all commercial uses, including concentrates. As shown in Example 3, the stirred wash stage typically increases Reb A purity from approximately 96% purity Reb A (purity after the first reflux stage and before the stirred wash stage) to 100% pure Reb A (after the stirred wash stage). If the uses of the final product can tolerate the residual bitterness of Reb A of less than 99% purity, the stirred wash stage can be omitted and the retentate from filtering the reflux mixture can be dried and used commercially. However, a stirred wash stage is preferred to eliminate all perceptible bitterness.

As shown in Examples 1 and 2, if the *Stevia* starting material is less than 85% Reb A, at least one additional reflux stage is typically required to produce 100% pure Reb A. To process *Stevia* starting material of less than RA85 purity, a first reflux stage is performed using the selected EtOH solvent, but the wet solids retentate from filtering the reflux mixture is typically used as starting material for a second reflux instead of being placed in a stirred wash. The processing parameters for the additional second reflux stage (and more additional reflux stages, as needed to achieve a target Reb A purity) are the same as for the first reflux stage described, including the EtOH formulation stage. Optionally, a stirred wash stage (but without drying the wet solids) can be performed between reflux stages, in which case the wet solids retentate from filtering the wash mixture ("intermediate stirred wash stage") is used as starting material for the following reflux stage. Intermediate stirred wash stages are sometimes needed when processing *Stevia* starting material of RA80 or lower quality.

For expediency, the selected EtOH solvent used in the first reflux can be used in the additional reflux stages. However, to further optimize yields, a starting material assay can be performed on samples taken from the wet solids retentate produced in the filtering step that concludes each reflux stage (if an intermediate stirred wash stage is inserted between reflux stages, the wet solids retentate from filtering an intermediate stirred wash stage wash mixture is used as starting material for the starting material assay). After the final reflux stage, a stirred wash stage is typically conducted (and then the ethanol purge and the drying stage), as described above, to produce up to 100% pure Reb A. Each additional reflux stage, however, decreases yields of final product. If the uses of the final product can tolerate the residual bitterness of Reb A of less than 99% purity, the number of reflux stages (and optional intermediate stirred wash stages) is selected to produce the target purity and yield required for the given uses.

Although a heating rate of 4° C./min. and a cooling rate of −1.8° C./min. are described, other cooling and heating rates obtainable with typical laboratory equipment may be used without significantly decreasing yield or purity of Reb A in the final product. Very high heating rates require vigorous agitation of the mixture to prevent burning or hydrolysis of the starting material. Heating and cooling rates obtainable may depend on batch size. For instance, force-cooling in a laboratory may be accomplished by setting a reaction flask on ice or in ice water; larger reaction volumes in a given flask size take longer to cool on ice or in ice water. Generally speaking, following a reflux, during optional standing steps, mixture temperatures that are lower than room temperature but higher than 0° C. (for mixtures containing water) and long standing times, will improve yields of Reb A, especially when processing lower quality *Stevia* starting material. During long standing times, especially with post-reflux mixture temperatures below room temperature, it is critical that the mixture be stirred to avoid gelling, crusting, or solidification of the mixture; if gelling, crusting, or solidification occurs, yield and/or purity may be adversely affected. If the post-reflux mixture is cooled and inadequately stirred during a standing time in excess of 12 hours, the mixture may gel, crust, or solidify; if this happens, some or all of the mixture may not thereafter be easily convertible into a pumpable slurry for further processing. Following the stirred wash, mixture temperatures below 0° C. and approaching the freezing point of ethanol can be used, Even when processing RA40 *Stevia* starting material, standing times after reflux or stirred wash that are longer than 96 hours provide little improvement in yield.

With a solvent of 5% to 15% water and the remainder ethanol, *Stevia* starting material immediately goes into solution with stirring. In an anhydrous ethanol solvent, however, *Stevia* starting material only goes into solution with heating, and both the yields and purity of Reb A in the final product are lower using anhydrous ethanol as a reflux solvent. With 5% to 15% water in the solvent, when the mixture of solvent and *Stevia* starting material reaches 50° C., Reb A begins to precipitate out of solution; in contrast, in an anhydrous ethanol solvent, however, when the mixture of solvent and *Stevia* starting material reaches 50° C., the *Stevia* starting material is still dissolving and precipitation of Reb A has not begun. After each reflux stage, rather than force-cooling the mixture after removal of heat, the mixture can simply be allowed to air cool to room temperature, but yields of Reb A are lower compared with force-cooling (even with longer standing times, e.g., 96 hours, after reaching room temperature). In other words, force cooling of a reflux mixture improves yields for lower quality *Stevia* starting materials.

Figure 7:
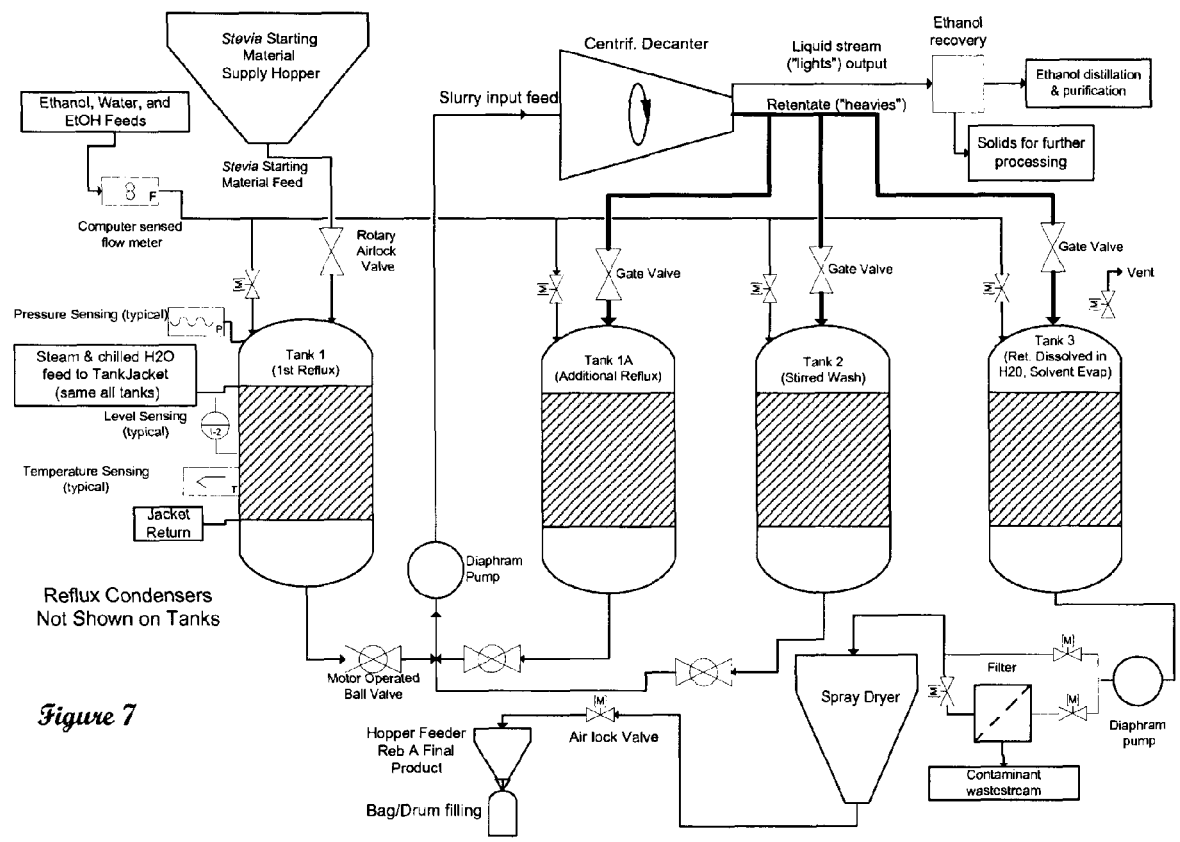
FIG. 7 shows an overall view of the apparatus used in the industrial embodiment of the invention.
Figure 8:
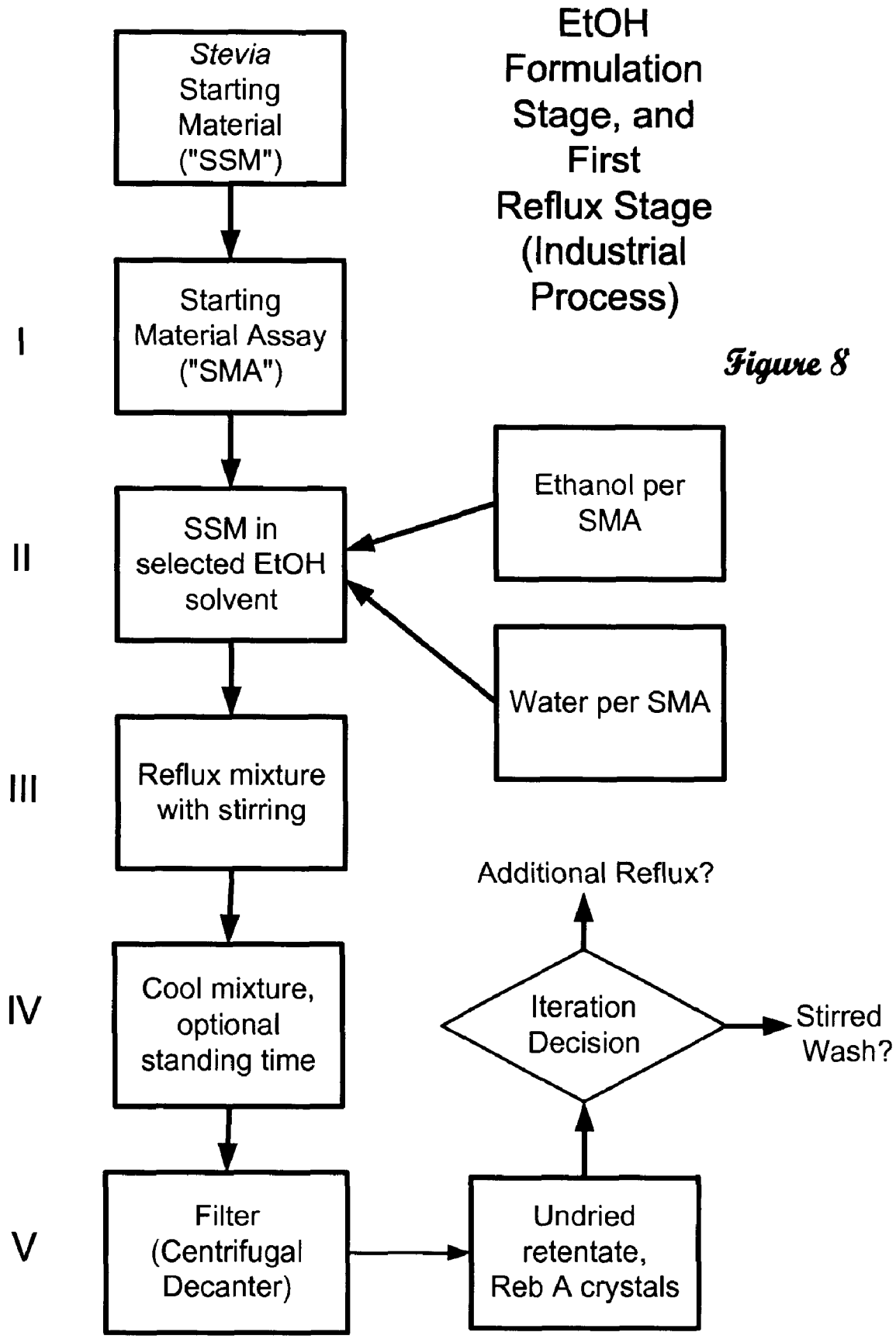
FIG. 8 shows the steps in the reflux stage of the industrial process.
Figure 9:
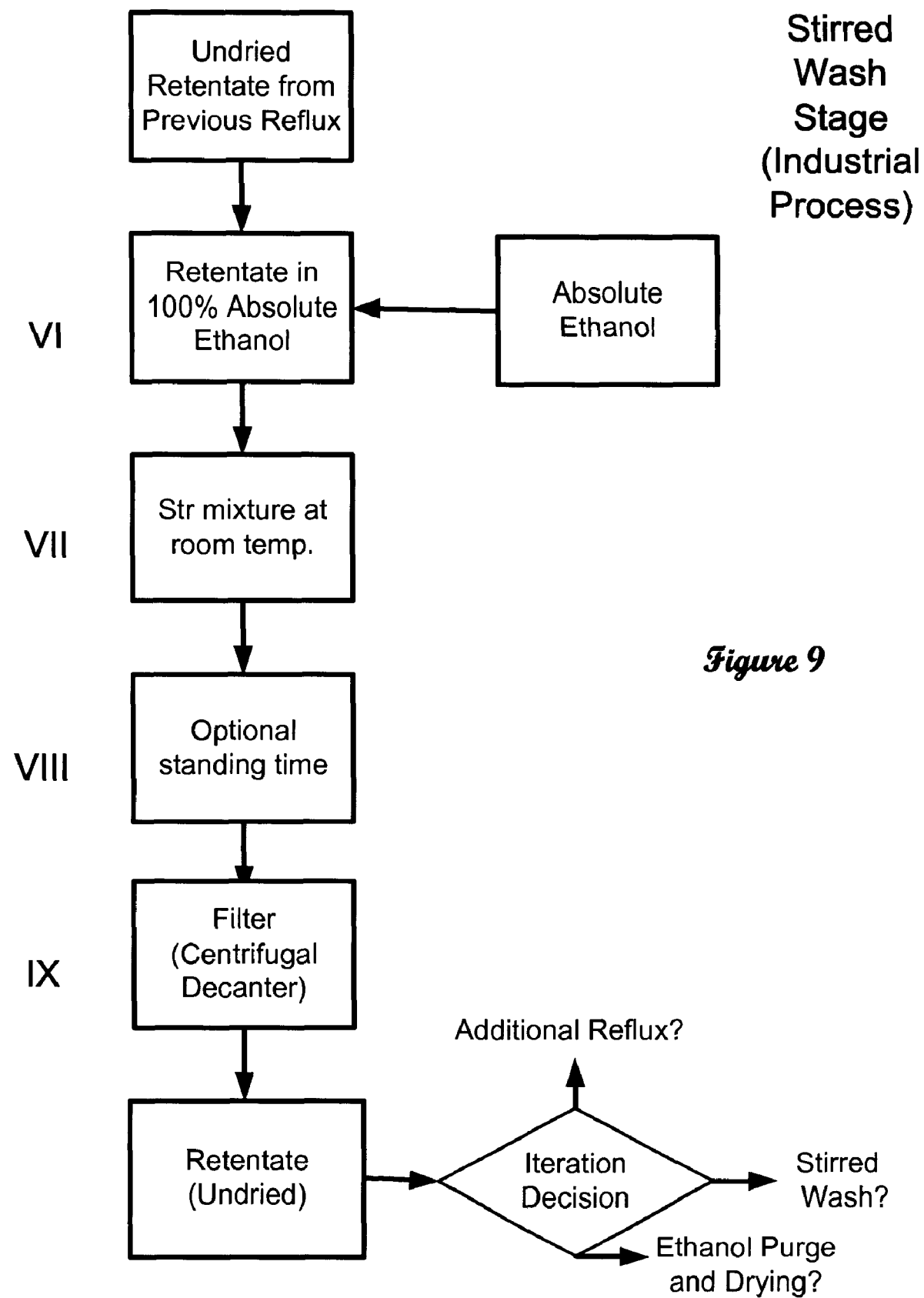
FIG. 9 shows the steps in the stirred wash stage of the industrial process.
Figure 10:
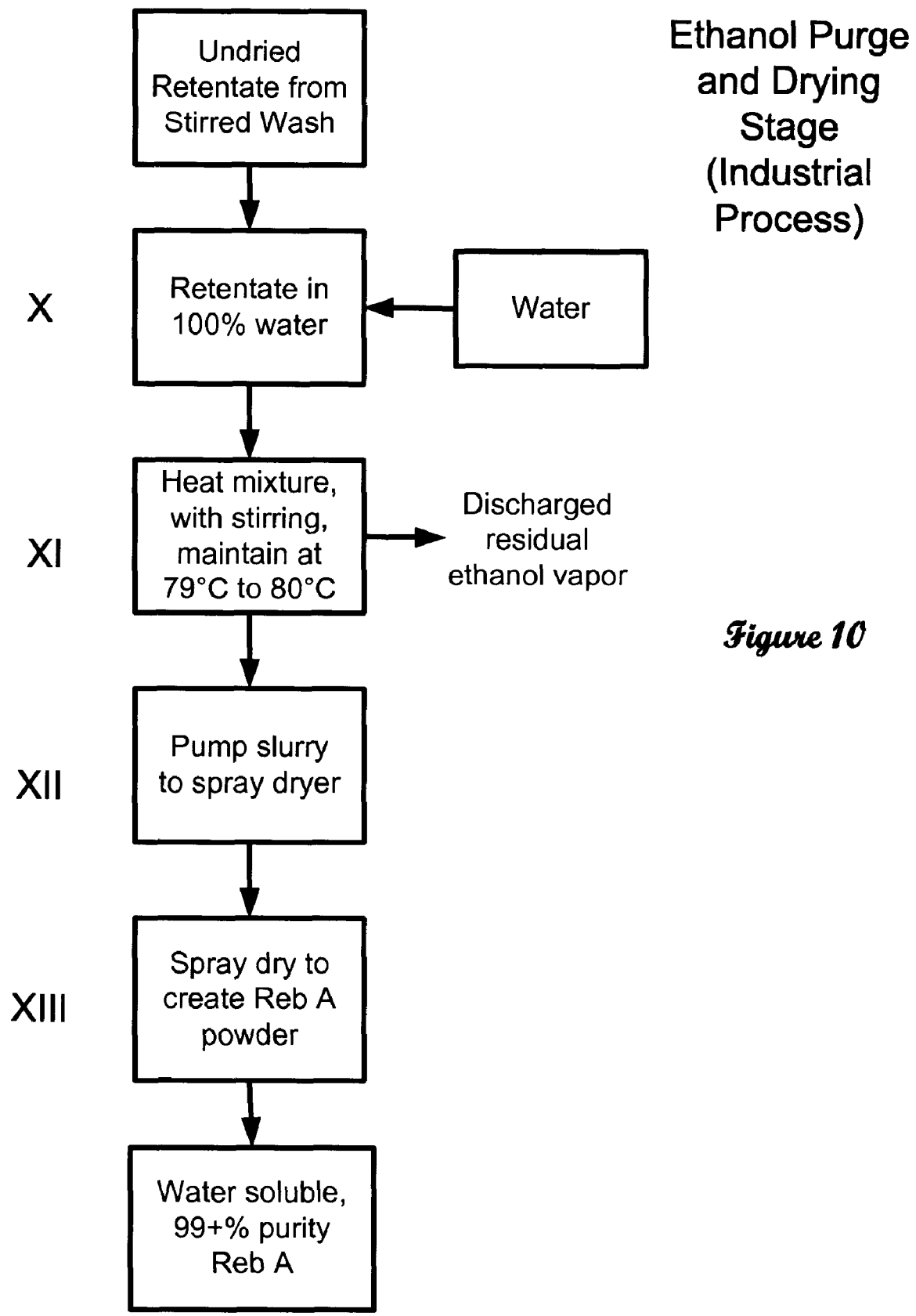
FIG. 10 shows the steps in the ethanol purge and drying stage of the industrial process.

FIG. 7 shows an overview of the apparatus used in the industrial embodiment of the invention. The basic industrial embodiment for processing higher quality *Stevia* starting material comprises three or four stages: an EtOH formulation stage, a reflux stage, optional stirred wash stage (typically required to produce 99+% purity Reb A), and an ethanol purge and drying stage. The decision points of whether to follow the first reflux with a single stirred wash stage or with one or more additional reflux stages (with or without more stirred wash stages) are shown in FIG. 1 (and other Figures) and denoted as "Iteration Decision". In embodiments that use lower quality *Stevia* starting material, at least one additional reflux stage is typically added before a final stirred wash stage to maximize purity of the Reb A final product. As shown in FIGS. 8 to 10 respectively, step I comprises the EtOH formulation stage, steps II to V comprise the reflux stage; steps VI to IX comprise the stirred wash stage; and steps X to XIII comprise the ethanol purge and drying stage of the industrial embodiment of the invention. In the industrial embodiment, steps X to XIII, the ethanol purge and drying stage, are also known as "purging the ethanol and drying the retentate."

As shown in FIG. 7, the typical apparatus to practice the industrial embodiment includes one or more jacketed, stainless steel pressure vessels ("tanks" or "mixing tanks"), each typically of 3,000 liter capacity, equipped for mixing (flexible scrapper blades), heating (steam in jacket), and cooling (chilled water in jacket), and equipped with inlet and outlet paths and a reflux condenser (not separately shown in FIG. 7). In all tank process steps other than step XI below, the outlet path of the reflux condenser attached to a mixing tank is connected back to the mixing tank. An adequately rated pressure vessel without a reflux condenser can be used in the industrial embodiment, but a reflux condenser is preferred because of the superior mixture agitation and reduction of mixture superheating. All tanks, shells, tubes, valves, motors, etc., are ASTM pressure vessel certified for use with explosive liquids and vapors. Each tank has: pressure and temperature sensors and flow and/or quantity indicators; powder hopper and feeder, with inlet flow metering; ethanol and water feeds with inlet flow metering; shut-off valves; and customary other fixtures known in the art of processing in pressure vessels, such as one or more centrifugal decanters (typically continuous flow models), membrane filters (optional), pumps, holding tanks, pumps, spray dryer, hopper feeder, pipes that interconnect the elements of the apparatus, filters, etc., and a process control system.

As shown in FIG. 8, step I in the industrial embodiment of the invention is a determination of the water to ethanol balance in the reflux solvent. The preferred means of determination of the selected EtOH solvent is to perform one to three iterations of the starting material assay, as described above and illustrated in FIGS. 4 and 5. An alternative means of determining the selected EtOH solvent is to use the reflux solvent approximation, as described above. The starting material assay is preferred, since the starting material assay provides the minimum, not just an approximation of, water content needed in the reflux solvent to produce (after the final stirred wash stage) 100% pure Reb A when using higher quality *Stevia* starting material. Given the large quantities of *Stevia* starting material, ethanol, and energy used in the industrial process, optimizing yields by optimizing the selected EtOH solvent is often critical to the profitability of a producer. Accordingly, the starting material assay is typically multiply iterated, as described above, to optimize the selected EtOH solvent for a given *Stevia* starting material (and optionally, for a given retentate before one or more additional refluxes). As discussed above, each starting material assay can optionally include, after the selected EtOH solvent is determined, a mass to volume ratio assay to determine the ratio of mass to volume of selected EtOH solvent that maximizes Reb A yield.

As shown in FIG. 8, after the EtOH solvent is selected, in an industrial embodiment of the invention, a producer-determined amount of the sampled batch is processed using the reflux and stirred wash stages (or, when processing lower quality *Stevia* starting materials, a one or more additional refluxes, each additional reflux stage with or without an intermediate stirred wash stage). Step II in the industrial process is to supply and mix ethanol and water in a first tank ("Tank 1") to produce a reflux solvent that is the selected EtOH solvent. The ethanol content is maintained throughout process steps II to IV at approximately +/−2% of the ethanol content in the selected EtOH solvent by capturing and cooling reaction vapors using a reflux condenser and returning the condensate to Tank 1. In step II, the *Stevia* starting material is added to and mixed with the selected EtOH solvent at a mass to volume ratio of 1 to 4 (*Stevia* starting material to selected EtOH solvent) or at the mass to volume ratio determined using the optional mass to volume ratio assay, as described above. In step III, while being continuously mixed in Tank 1, the mixture is heated (steam fed to jacket of Tank 1, typical heating rate of 1° C./min.) to 79° C. All reactions in the typical industrial embodiment are at one atmosphere of pressure.

After the Tank 1 mixture has reached 79° C., mixing during reflux is continued for 1 hour while maintaining the reflux mixture temperature between 79° C. to 80° C. (the ethanol in Tank 1 boils and is recovered through the reflux condenser). In Step III, as the reflux mixture temperature increases above 50° C., Reb A typically begins to precipitate out of solution. If Tank 1 is not filled to maximum mixing capacity, a thick creamy substance (primarily precipitating Reb A crystal) may form and line the interior surface of Tank 1; scraping blades are preferably used to return the creamy substance to the mixture. In step IV, the refluxed mixture is cooled (chilled water (4° C.) fed to Tank 1 jacket, typical cooling rate of −0.3° C./min.) to a temperature between 4° C. to 20° C., typically 14° C. In step IV, when processing *Stevia* starting material of less than RA80 quality, the mixture is typically held chilled at constant temperature (typically 14° C.), while being mixed, to improve yield. In such cases, the longer the chilled standing period, the greater is the recovery of precipitated Reb A, up to approximately 96 hours of standing time. During this standing time, mixing blades scrape the interior surface of Tank 1 to maintain a slurry in the bottom of Tank 1. If cooled and unstirred during standing time, the mixture may become gelatinous or even crusty; if the mixture become gelatinous or crusty, the mixture may not thereafter be convertible into a pumpable slurry for further processing without adversely affecting yield and/or purity. In step IV, when processing higher quality *Stevia* starting material, standing time is typically not necessary after cooling the reflux mixture (typically to 14° C.). Batch processing of *Stevia* starting materials, as described above and below for Tank 1, can be performed concurrently in other available tanks. Typically two or more tanks are used in a commercial production facility, with batches phased based on workforce and product demand Next, enough absolute ethanol (anhydrous ethanol) is added to the contents of Tank 1 to create a pumpable slurry. Once the chilled slurry in Tank I becomes pumpable (pumpability depends upon the type of pump; typically a diaphragm pump handles a more viscous fluid than an impeller pump), the slurry in Tank 1 is pumped to a continuous-flow, centrifugal decanter. The centrifugal decanter is supplied with the slurry stream, and in step V, the ethanol is decanted to the "lights" discharge outlet, and the retentate is fed (typically, a gravity feed) out the retentate, or "heavies", discharge outlet. Typically in large scale production, the "lights" discharge stream is pumped through a means (e.g., a membrane filter or falling film evaporator) of separating the small solids from the ethanol in the "lights" discharge stream. The recovered ethanol is typically distilled and reused. The small solids captured by the separating means are typically returned to a mixing tank for further processing (e.g., in a stirred wash stage or additional reflux stage).

Even though a centrifugal decanter is not a true filter, it performs a filter-like function of separating "lights" and "heavies" (i.e., separating liquid and small solids, or lights, from heavier particles, or heavies). Therefore, the use of a centrifugal decanter in the invention is called "filtering". Filtering requires that the filtering means separate particles with an axis or diameter approximately greater than 2.0 μm, more preferably greater than 1.5 μm; and most preferably equal to or greater than 0.1 μm from the mixture being filtered. Other apparatus that separate liquids from solids, such as membrane filters and falling film evaporators, can be used instead of a centrifugal decanter, but for a given investment in apparatus, the throughput of alternative technology is often significantly lower compared with the throughput of a centrifugal decanter. The filtering means is selected must be appropriate for the volume of mixture to be filtered and throughput required. For this reason, centrifugal decanters are typically favored over membrane filters and falling film evaporators for use in filtering refluxed mixtures and stirred wash mixtures in the industrial embodiment of the invention, since centrifugal decanters have much higher throughput, far fewer clogging problems, and cost less compared with alternative technologies.

As shown in FIG. 9, in step VI, the wash stage commences by supplying an available tank ("Tank 2") with the wet solids from the retentate discharge outlet of the centrifugal decanter and 100% absolute ethanol typically at or near a ratio of 1 gram of wet solids to 4 mls of ethanol ("wash mixture"). Ratios of wet solids retentate to ethanol below 1:3.5 (m/v) in a stirred wash stage may be so viscous that processing is impaired. Ratios of wet solids retentate to ethanol above 1:4 (m/v) in a stirred wash stage typically produce negligible improvement in Reb A purity and often decrease Reb A yield. Therefore, a mass to volume ratio of wet solids retentate to ethanol of 1:4 or very close thereto in a stirred wash stage is the most preferred ratio when using higher quality *Stevia* starting materials. In Step VII, the wash mixture is stirred, using the mixing blades of Tank 2, for 15 minutes without further heating or cooling of the wash mixture (i.e., at ambient temperature). The mixture may be allowed to stand (step VIII) to improve yields when using lower quality *Stevia* starting materials. After stirring and optional standing time, in step IX, the wash mixture in Tank 2 is pumped to a continuous-flow, centrifugal decanter. The centrifugal decanter is supplied with the wash mixture as input, the ethanol is decanted to the "lights" discharge outlet, and the retentate is fed (typically, a gravity feed) out the "heavies" (retentate) discharge outlet. Chilling the wash mixture during the stirred wash, and allowing the wash mixture to stand (step VIII), typically with mixing, after completion of stirred wash and before decanting, marginally increases yields when processing higher quality *Stevia* starting material, but significantly increases yields when processing lower quality *Stevia* starting material.

As shown in FIG. 10, the ethanol purge and drying stage, in order to produce final product as a powder, in step X retentate from the decanter is fed (typically, a gravity feed) into an available tank ("Tank 3") and combined with water such that the ultimate volume is approximately twice the mass of the retentate supplied to Tank 3. For example, to 500 kg of retentate, enough potable (preferably, filtered) water is added to produce approximately 1,000 liters final volume of mixture ("water mixture"). In step XI, the contents of Tank 3 are heated (heating rate of 1° C./min.) to 79° C. in a vessel equipped with a vapor discharge outlet, then maintained at between 79° C. to 80° C., and mixed to evaporate residual ethanol in the mixture. Mixing the contents of Tank 3 at that temperature (the boiling point of ethanol) causes any ethanol remaining in the mixture to evaporate; the ethanol in the discharged vapor is preferably captured and recycled (but can be vented as a waste stream out of Tank 3). The mixing continues until the ethanol content of the mixture is safe for spray-drying. The manufacturer of the spray dryer used in step XIII specifies a maximum content of flammables in liquids to be spray-dried, which is the upper limit of ethanol content fed from Tank 3 to a spray dryer. Alternate means of drying that do not require pre-removal of the solvent can be used, such as an explosion-proof spray dryer, but such alternate means may require more operator attention. An explosion-proof spray dryer would shorten production time and reduce energy consumption. As described in Example 6, at industrial scale (e.g., 500 kgs of *Stevia* starting material), boiling off the ethanol before spray-drying can require ten or more hours to purge the ethanol.

In step XII, the contents of Tank 3 are maintained between 60° C. and 99° C. (preferably between 79° C. to 80° C.) while pumping the contents of Tank 3 to a spray dryer (step XIII). Since the *Stevia* starting material is refluxed in EtOH solvent, it is doubtful that any pathogens would survive the reflux (microbial content in final product is undetectable, based on third party lab tests). Before spray-drying, the mixture can optionally be pumped trough a membrane filter or equivalent means of separation to remove any particulate contaminants. The spray dryer typically discharges through an automatically controlled airlock valve into a feed hopper (typically equipped with a screw-feed bag loader). The solids in the feed hopper are the final product, water soluble, 99+% purity Reb A, in powder form. As shown in Example 4 (a two reflux, industrial process) below, 68% of the *Stevia* starting material by dry weight was recovered when processing RA89.95 *Stevia* starting material, and the recovered solids were 99+% Reb A. Example 4 represents a recovery of 75.25% of the Reb A in the *Stevia* starting material. As shown in Example 6 (a single reflux with single stirred wash process using RA83.14 *Stevia* starting material) below, 59.04% of the *Stevia* starting material by dry weight was recovered, and the recovered solids were 99+% Reb A. Example 6 represents a recovery of 70.59% of the Reb A in the *Stevia* starting material.

The 99+% purity Reb A final product of the industrial embodiment typically has solubility in water of 33% (1 gram in 3 mls final volume). As shown in Example 4, the stirred wash stage typically increases Reb A purity from approximately 96% purity Reb A (purity after the first reflux stage and before the stirred wash stage) to 100% pure Reb A (after the stirred wash stage). If the uses of the final product can tolerate the residual bitterness of Reb A of less than 99% purity, e.g., for use in pickling or in flavor modification below the sweetness threshold, the stirred wash stage can be omitted and the retentate from filtering the reflux mixture can be dried and used commercially. However, a stirred wash stage is preferred to eliminate all perceptible bitterness. Solubility in water of approximately 33% is adequate for all commercial uses, including concentrates.

As shown in Examples 1, 5, and 7 below, if lower quality *Stevia* starting material is used, at least one additional reflux stage is typically required to produce 99+% purity Reb A (final product of the stirred wash stage). To process *Stevia* starting material using two reflux stages, a first reflux stage is performed using the selected EtOH solvent, but the wet solids retentate from filtering the reflux mixture is used as starting material for a second reflux instead of being placed in a stirred wash. A decision to conduct one or more additional refluxes and/or stirred washes is called an "iteration decision", and denoted in several of the Figures as "Iteration Decision". The processing steps for an additional reflux stage (and any more additional reflux stages, as needed to achieve a target Reb A purity), as shown in FIG. 6, are described above, including one or more EtOH formulation stages.

In FIG. 6, the mix, heat, reflux, cool, and stand steps (i.e., steps C' to E') of an additional reflux stage would typically be performed in Tank 1A (as shown in FIG. 7). Optionally, an intermediate stirred wash stage can be performed between reflux stages, in which case the wet solids retentate from decanting the intermediate stirred wash mixture is used in an optional EtOH formulation stage (step B') or otherwise as starting material for an additional reflux stage (steps C' to E'). After cooling, the mixture is filtered (step F'). An additional reflux stage is followed either by another additional reflux stage, a stirred wash stage, or by an ethanol purge and drying stage. Iterations of the starting material assay are preferably done at the beginning of each additional reflux stage to monitor the improvement in Reb A purity. Generally, if retentate Reb A purity is over 96%, after a reflux stage, then a stirred wash stage and an ethanol purge and drying stage will produce 99+% purity Reb A final product.

Typically, the selected EtOH solvent used in the first reflux is also used in any additional reflux stages. However, to further optimize yields, an EtOH formulation stage can be performed on samples taken from the wet solids retentate produced in the decanting step that concludes each reflux stage (if an intermediate stirred wash stage is inserted between reflux stages, the wet solids retentate from decanting an intermediate stirred wash stage is used as starting material for the EtOH formulation stage). After the final reflux stage in the industrial process, a stirred wash stage and the ethanol purge and drying stage are conducted, as described above, to produce 99+% purity Reb A. Each additional reflux stage, however, decreases yields of final product.

Although a heating rate of 1° C./min. and a cooling rate of −0.3° C./min. are described in the industrial process, other cooling and heating rates obtainable with typical industrial equipment may be used without significantly decreasing yield or purity of Reb A in the final product. Very high heating rates require vigorous agitation of the mixture to prevent burning or hydrolysis of the starting material. Heating and cooling rates obtainable may depend on batch size, pressurized heating and cooling, and (in the case of cooling) the use of refrigerants instead of chilled water. For instance, force-cooling may be accomplished by using refrigerants with temperatures below 0° C. (at least during the initial cooling period with vigorous mixing while the mixture temperature is considerably higher than 0° C.) in the pressure vessel jackets. Mixture temperatures during optional standing steps after the first or additional reflux steps that are lower than 4° C. but higher than 0° C. (which avoids ice formation in the mixture) and long standing times will improve yields of Reb A slightly, especially when processing *Stevia* starting material of less then RA80 purity. However, even when processing RA40 *Stevia* starting material, standing times after reflux or stirred wash that are longer than 96 hours provide little improvement in yield.

Rather than use reflux condensers in the laboratory and industrial processes, other methods (e.g., venting the vapor and supplying fresh ethanol and water, or other apparatus to capture and condense solvent vapor and return it to the mixture) can be employed to maintain the approximate desired concentration of mixed components.

Instead of EtOH, the reflux solvent used in the invention can be hydrous alkanols other than EtOH, but purities and yields decrease if other hydrous alkanols are substituted for EtOH. Likewise, the stirred wash solvent can be alkanols other than ethanol. The use of other hydrous alkanols as the reflux solvent, and other alkanols as the stirred wash solvent, may result in akylated contaminants incompatible with use in compositions for human consumption. If other hydrous alkanols are used, the starting material assay (or reflux solvent approximation), and optional mass to volume ration assay, are performed to determine the water content of the reflux solvent for a given reflux and *Stevia* starting material and the mass to solvent ratio, respectively.

As described above, the minimum number of reflux stages and stirred wash stages needed to achieve a target Reb A purity is determined empirically using permutations of refluxes (with mass to solvent ratios sometimes higher than 1 to 4 for lower quality *Stevia* starting material) and stirred washes for a given *Stevia* starting material and target Reb A purity. As a general rule, when a single reflux stage and one or two stirred wash stages do not produce 99+% purity Reb A, a mass to volume ratio assay is included in one or more EtOH formulation stages. As noted above, using higher quality *Stevia* starting material in the invention typically provides 99+% purity Reb A using a single reflux and single stirred wash and a mass to volume ratio of 1 to 4. For lower quality *Stevia* starting material, with a target purity of 99+% purity Reb A final product, a preferred approach is to use a mass to volume ratio of 1 to 4 and as many refluxes as necessary ("selected reflux iteration count") to obtain about a 96% to 98% purity Reb A final product in an EtOH formulation stage. An EtOH formulation stage with the selected EtOH iteration count, plus a stirred wash stage, is then performed to determine if adding a final stirred wash will provide the target purity; if not, the options are to add another reflux stage or to adjust the mass to solvent ratio (using a mass to solvent ratio assay) in one or more EtOH formulation stages, and again determine if the target purity has been reached. As Example 7 shows, if the target purity is 100% purity Reb A final product using RA82.3 *Stevia* starting material, and the target purity cannot be reached using two refluxes, a single stirred wash, and a mass to volume ratio of 1:4, increasing the mass to volume ratio in the refluxes to 1:6 can provide the target purity. Lower quality *Stevia* starting material is considerably cheaper than higher quality *Stevia* starting material. In locales in which the cost of ethanol and energy is low, lower quality *Stevia* starting material can be processed to 99+% purity Reb A cost effectively. In countries in which the cost of ethanol and energy is high, higher quality *Stevia* starting materials are typically required for cost effectiveness.

A reflux mixture temperature of between 79° C. to 80° C. typically produces the shortest acceptable reflux time (typically one hour). Reflux mixture temperatures lower than 79° C. can be used; however, such lower reflux mixture temperatures typically require longer durations of reflux and produce considerably lower yields of Reb A. For example, as the reflux mixture temperature is increased above 50° C., the reflux mixture becomes opalescent as Reb A begins to precipitate; the reflux mixture could be maintained in the 50° C. to 60° C. range, and depending on duration of reflux, could reduce heating costs, but the yield of Reb A would be considerably reduced compared with a reflux mixture temperature of between 79° C. to 80° C. In some locales, however, e.g., locales using solar heating, only lower reflux mixture temperatures may be feasible.

Uses of the Reb A Product. The 99+% purity Reb A produced by the invention ("Reb A Product"), can be used as a sole sweetener of food, beverage, medicine, tobacco, pharmaceutical, and personal care products, or mixed with other sweeteners in such products (i.e., as a "co-sweetener"). More than one sweetener is typically used to obtain specific taste profiles and/or physical properties. Such sweeteners include conventional sweeteners (cane sugar, beet sugar, honey, syrups, and other "natural" sweeteners) and high-intensity sweeteners (cyclamates, saccharin, sucralose, aspartame, *Stevia*, and other chemically produced and/or natural high-intensity sweeteners).

To modify the perceived sweetness of orally consumable compositions containing the Reb A Product, Reb A Product can be modified by the addition of taste modifying moieties, such as galactosides. For instance, 13-1,4-galactosyl can be substituted on the Reb A Product using a 13-1,4-galactosyl transferase enzyme in reactions known in the art. The 99+% purity Reb A produced by the invention that has been modified by one or more functional groups to produce a compound with pleasant sensory perceptions when used in orally consumed compositions is included in the term "Reb A Product".

For use as a co-sweetener, the Reb A Product can be used in ways known in the art of sweeteners (e.g., steam, ethanol, or alkanol aerosolized Reb A Product vapor-deposited on a co-sweetener) to coat or permeate other solid sweeteners, such granular and powdered sugar and artificial sweeteners, to be mixed as a separate powder with such solid sweeteners, to be co-crystallized with other solid sweeteners, or to be suspended or dissolved in liquid sweeteners, such as corn syrup and honey. Commercially available spray dryers used in the ethanol purge and drying stage of the industrial embodiment can typically be configured to produce a particulate size of Reb A Product appropriate for an intended use.

The term "flavor" or "flavor characteristic", as used herein, is the combined sensory perception of the components of taste, odor, and/or texture. The term "enhance", as used herein, includes augmenting, intensifying, accentuating, magnifying, and potentiating the sensory perception of a flavor characteristic without changing the nature or quality thereof. The term "modify", as used herein, includes altering, varying, suppressing, depressing, fortifying and supplementing the sensory perception of a flavor characteristic where the quality or duration of such characteristic was deficient.

In the art of flavoring foodstuffs and medicinal compositions, there is a continuing need for compositions which can modify and improve the flavor of such materials, because acceptance and demand for foodstuffs and medicinal products is generally related to the sensory perception of them. In the art of flavoring oral hygiene compositions, such as mouthwash and toothpaste, and in the art of flavoring chewing compositions, such as chewing tobacco, snuffs and chewing gum, there is a need to improve the flavor characteristics of such chewing compositions with flavor modifiers or enhancers which are non-cariogenic and do not support the growth of tooth decay producing streptococci, lactobaccilli, or the like. Likewise, there is need to improve the flavor characteristics of smoking compositions.

The term "orally consumable composition" includes foodstuffs, medicinal compositions, smoking compositions, chewing compositions and oral hygiene compositions, including mouthwashes and toothpastes. The term "foodstuff" includes both solid and liquid ingestible materials which usually do, but need not, have a nutritional value and are intended for consumption by man or animal. Representative examples of foodstuff include coffee, teas, herbal teas, baked goods, natural and synthetic flavors, spices, condiments, soups, stews, convenience foods, beverages (both carbonated and non-carbonated), dairy products, candies, vegetables, cereals, fruits, fruit drinks, snacks, cocoa products, chocolates, animal feed, and the like. The term "medicinal composition" includes solids, gases and liquids which are ingestible materials having medicinal value, such as cough syrups, cough drops, medicinal sprays, vitamins, and chewable medicinal tablets. The term "chewing compositions" include chewing tobacco, smokeless tobacco, snuff, chewing gum and other compositions which are masticated and subsequently expectorated. Chewing gum includes compositions which comprise a substantially water-insoluble, chewable gum base, such as chicle or substitutes therefor, including jetulong, guttakay rubber or certain comestible natural synthetic resins or waxes. The term "oral hygiene compositions" includes mouthwashes, mouth rinses, toothpastes, tooth polishes, dentifrices, mouth sprays, and mouth refreshers. The term "smoking composition", as used herein, includes cigarette, pipe and cigar tobacco, and all forms of tobacco such as shredded filler, leaf, stem, stalk, homogenized leaf cured, reconstituted binders, and reconstituted tobacco from tobacco dust, fines, or other sources in sheet, pellet or other forms. "Smoking compositions" also include tobacco substitutes formulated from non-tobacco materials, such as representative tobacco substitutes described in U.S. Pat. Nos. 3,529,602, 3,703,177 and 4,079,742 and references cited therein.

In accordance with one embodiment of this invention, an orally consumable composition having flavor enhanced or modified by the Reb A Product is provided. The Reb A Product can modify or enhance flavor characteristics that are sweet, fruity, floral, herbaceous, spicy, aromatic, pungent, "nut-like" (e.g., almond, pecan), "spicy" (e.g., cinnamon, clove, nutmeg, anise and wintergreen), "non-citrus fruit" flavor (e.g., strawberry, cherry, apple, grape, currant, tomato, gooseberry and blackberry), "citrus fruit" flavor (e.g., orange, lemon and grapefruit), and other useful flavors, including coffee, cocoa, peppermint, spearmint, vanilla and maple.

In accordance with one variation of this embodiment, an orally consumable composition comprises a Reb A Product in an amount effective to sweeten or to modify or enhance the taste, odor and/or texture of the orally consumable composition.

The terminology "amount effective" or "effective amount" means an amount that produces a sensory perception. The use of an excessive amount of a Reb A Product will produce sweetness that may not be desired for flavor modification or enhancement, just as too much sugar can be added to a foodstuff or beverage. The amount of Reb A Product employed can vary over a relatively wide range, depending upon the desired sensory effect to be achieved with the orally consumable composition and the nature of the initial composition.

Reb A Product can be added to an orally consumable composition by admixing the Reb A Product with the orally consumable composition or admixing the Reb A Product with a component of the orally consumable composition.

The Reb A Product can be used in tobacco and tobacco-related products selected from the group comprising cigarettes, cigars, snuffs, chewing tobacco, other tobacco goods, filters, smoking papers, and other smoking compositions. A smoking composition having a sweetened, enhanced, or modified flavor comprises a smoking filler material selected from the group consisting of tobacco, reconstituted tobacco, non-tobacco substitutes and mixtures thereof, and containing an effective amount of Reb A Product. "Containing" means both being included as an ingredient and being adsorbed to a material. In one variation of this embodiment, the smoking composition comprises a filter means containing a Reb A Product. The term "filter means", as used herein, includes a smoking device means such as a cigar or cigarette holder having a filtering or flavoring module incorporated therein and includes acetate, cotton, charcoal and other fiber, flake or particle filtering means. In another variation of this embodiment, the smoking composition comprises a wrapper means containing a Reb A Product. In one variation of this embodiment of this invention, 0.003 to 0.30 parts by weight of a Reb A Product is added to 100 parts by weight of the smoking filler material. In a preferred variation of this embodiment of this invention, 0.015 to 0.30 parts by weight of a Reb A Product is added to 100 parts of a weight of a smoking filler material.

Those skilled in the art of flavoring tobacco understand that the effective amount of the Reb A Product added to a smoking composition may depend upon the method in which the Reb A Product is added to the smoking composition and to which portion of the smoking composition Reb A Product is added. Reb A Product can be added directly to the smoking filler material, to the filter means, or to the wrapper means of a smoking composition. Reb A Product can be added to a filter means of a smoking composition by any manner known to those skilled in the art of flavoring filter means, including but not limited to, incorporating the Reb A Product among the fibers, flakes or particles of a filter means, filling the Reb A Product between two or more layers of fibers of a fiber filter means to form a triple filter means, or inserting the Reb A Product into a smoking device means, such as a cigarette holder.

It is apparent to those skilled in the art that only a portion of the smoking filler material or filter means need be treated with a Reb A Product, since blending or other operations may be used to adjust the final or ultimate smoking composition within the effective or desired ranges of concentration of Reb A Product. In addition to Reb A Product, other flavorings or aroma additives known in the smoking composition flavoring art may be used with Reb A Product and added along with Reb A Product to the smoking composition. Representative flavorings used in the smoking composition flavoring art include ethyl acetate, isoamyl acetate, propyl isobutyrate, isobutyl butyrate, ethyl butyrate, ethyl valerate, benzyl formate, menthol, limonene, cymene, pinene, linalool, geraniol, citroneilol, citral, peppermint oil, orange oil, coriander oil, lemon oil, borneol, cocoa extract, tobacco extract, licorice extract and fruit extractives.

Reb A Product, in its purified state after spray drying, is generally a fine powder, having a particle size in the range of about 1 to 100 microns. Fine powders are difficult to handle and difficult to admix with orally consumable compositions, such as tea leaves, tobacco products, herb leaves, coffees and other orally consumable compositions. Also, generally, only a relatively small amount of Reb A Product is used with an orally consumable composition when the Reb A Product is used as a flavor modifier or enhancer, sweetener, or co-sweetener.

In accordance with another embodiment of this invention, a process for adding Reb A Product to an orally consumable composition comprises admixing Reb A Product with a carrier to form a Reb A Product-carrier mixture. Preferred carriers include water, ethanol, other alkanols used in food processing, or mixtures thereof. The Reb A Product solution so formed is contacted with an orally consumable composition, and the carrier is removed from the orally consumable composition by evaporation, or otherwise, and the Reb A Product residues deposited with the orally consumable composition. This process is particularly useful for adding Reb A Product to tea leaves, herbal plant leaves, and other sweeteners, particularly granular sucrose (table sugar).

In accordance with still another embodiment of this invention, a liquid filter material, suitable for use with an orally consumable composition, is prepared with Reb A Product. The term "liquid filter", as used herein, refers to a porous or semi-porous filter material used for preparation of an orally consumable composition such as a tea bag, a coffee filter or a filter disk. The term "filter disk" refers to a porous or semi-porous inactive article added to an orally consumable composition for the purposes of acting as a vehicle for the addition of a flavoring or sweetening composition to the orally consumable composition. A process for preparing a liquid filter comprising a filter material and Reb A Product is typically by admixing Reb A Product with a carrier to form a Reb A Product-carrier mixture; contacting the Reb A Product-carrier mixture with the filter material; and removing the carrier from the filter material thereby depositing a Reb A Product residue on the filter material.

The Reb A Product can be used in beverages, broths, and beverage preparations selected from the group comprising carbonated, non-carbonated, frozen, semi-frozen ("slush"), non-frozen, ready-to-drink, concentrated (powdered, frozen, or syrup), dairy, non-dairy, herbal, non-herbal, caffeinated, non-caffeinated, alcoholic, non-alcoholic, flavored, non-flavored, vegetable-based, fruit-based, root/tuber/corm-based, nut-based, other plant-based, cola-based, chocolate-based, meat-based, seafood-based, other animal-based, algae-based, calorie enhanced, calorie-reduced, and calorie-free products, optionally dispensed in open containers, cans, bottles or other packaging. Such beverages and beverage preparations can be in ready-to-drink, ready-to-cook, ready-to-mix, raw, or ingredient form and can use the Reb A Product as a sole sweetener or as a co-sweetener.

The Reb A Product can be used in foods and food preparations (e.g., sweeteners, soups, sauces, flavorings, spices, oils, fats, and condiments) selected from the group comprising dairy-based, cereal-based, baked, vegetable-based, fruit-based, root/tuber/corm-based, nut-based, other plant-based, egg-based, meat-based, seafood-based, other animal-based, algae-based, processed (e.g., spreads), preserved (e.g., meals-ready-to-eat rations), and synthesized (e.g., gels) products. Such foods and food preparations can be in ready-to-eat, ready-to-cook, ready-to-mix, raw, or ingredient form and can use the Reb A Product as a sole sweetener or as a co-sweetener.

The Reb A Product can be used in candies, confections, desserts, and snacks selected from the group comprising dairy-based, cereal-based, baked, vegetable-based, fruit-based, root/tuber/corm-based, nut-based, gum-based, other plant-based, egg-based, meat-based, seafood-based, other animal-based, algae-based, processed (e.g., spreads), preserved (e.g., meals-ready-to-eat rations), and synthesized (e.g., gels) products. Such candies, confections, desserts, and snacks can be in ready-to-eat, ready-to-cook, ready-to-mix, raw, or ingredient form, and can use the Reb A Product as a sole sweetener or as a co-sweetener.

The Reb A Product can be used in prescription and over-the-counter pharmaceuticals, assays, diagnostic kits, and therapies selected from the group comprising weight control, nutritional supplement, vitamins, infant diet, diabetic diet, athlete diet, geriatric diet, low carbohydrate diet, low fat diet, low protein diet, high carbohydrate diet, high fat diet, high protein diet, low calorie diet, non-caloric diet, oral hygiene products (e.g., toothpaste, mouthwash, rinses, floss, toothbrushes, other implements), personal care products (e.g., soaps, shampoos, rinses, lotions, balms, salves, ointments, paper goods, perfumes, lipstick, other cosmetics), professional dentistry products in which taste or smell is a factor (e.g., liquids, chewables, inhalables, injectables, salves, resins, rinses, pads, floss, implements), medical, veterinarian, and surgical products in which taste or smell is a factor (e.g., liquids, chewables, inhalables, injectables, salves, resins, rinses, pads, floss, implements), and pharmaceutical compounding fillers, syrups, capsules, gels, and coating products.

The Reb A Product can be used in consumer goods packaging materials and containers selected from the group comprising plastic film, thermoset and thermoplastic resin, gum, foil, paper, bottle, box, ink, paint, adhesive, and packaging coating products.

The Reb A Product can be used in goods selected from the group comprising sweeteners, co-sweeteners, coated sweetener sticks, frozen confection sticks, medicine spoons (human and veterinary uses), dental instruments, pre-sweetened disposable tableware and utensils, sachets, edible sachets, pot pourris, edible pot pourris, hotch potches, edible hotch potches, artificial flowers, edible artificial flowers, clothing, edible clothing, massage oils, and edible massage oils.

EXAMPLES

HPLC Method

High performance liquid chromatography ("HPLC") was used to determine the purity of the final products produced by the methods of the invention. In the HPLC analysis method used in the Examples and in the description above, 0.1 grams of dried solids (e.g., the final product produced using the invention) is dissolved in 25 mls of 50% acetonitrile/50% water to create a sample. The sample is passed through a 0.45 µm nylon filter and 10 µl of filtrate injected into the HPLC injection port. The HPLC apparatus comprises a Shimadzu LC-10AS pump (Shimadzu North America, www.ssi.shimadzu.com), a Shimadzu SCL-10A controller and a Shimadzu SPD-10A variable wavelength detector. Raw data was collected on a Shimadzu CR501 Chromatopac integrator. A 4.2 mm i.d.×250 mm, 10 µm amine column was used (Alitech and Associates Inc., www.alltech.com) with an isocratic mobile phase consisting of 72.5% acetonitrile/27.5% water and a flow rate of 0.8 ml/min. Peaks were detected at 210 nm. Glycosides (stevioside and rebaudioside A) were quantified by comparison with a standard linear regression curve (y=mx+b) constructed from known concentrations of either stevioside (Chromadex Catalog No. ASB-00019351) or rebaudioside A (Chromadex Catalog No. ASB-00018226), respectively. The reference standards were used to analyze *Stevia* starting materials and solids produced by the invention. Stevioside and rebaudioside C were at the lower limits of detection, as described below, in the final product produced using the invention. The final product described in the invention has a higher purity than the current primary analytical standard for rebaudioside A, which has a certified purity of 98.7%. (Chromadex, Inc., Santa Ana, Calif., www.chromadex.com) The Chromadex standard was established in approximately 2002. The higher purity of the Reb A produced by the invention arises primarily from use of the EtOH formulation stage and a selected EtOH solvent, as described above. The phrase "100% pure Reb A" means that the chromatograph from the above-described high performance liquid chromatographic ("HPLC") analysis of a sample of final product produced using the invention shows miniscule blips (by retention time) of stevioside and rebaudioside C, a single strong peak of Reb A, and the HPLC integrator reports a value equal to or greater than the lowest value (typically, 98.7%) at 210 nm reported by the HPLC integrator for a sample of only the Chromadex reference standard for pure Reb A. Many Reb A reference standards for purity in general use prior to 2002 have been found to overstate Reb A purity; for instance, it is believed that the standard in common use in Canada before 2002 overstates Reb A purity by approximately 6% compared with analytic results using the Chromadex standard.

Since absorption at 210 nm in an HPLC apparatus varies based on the nature of the eluted compound and the compound's chromophore(s), using analytic methods other than standard linear regression curves constructed from reference compounds of known purity (e.g., Chromadex Catalog No. ASB-00018226) will produce erratic results.

Example 1

Example 1. Two reflux stages using a series of test solvents followed by an absolute ethanol reflux.

Example 1 demonstrates the effect of water content in reflux solvent on solids yield and rebaudioside A purity. In Example 1, a series of six solvents was formulated containing 0%, 2%, 4%, 6%, 8%, and 10% water and the remaining percentage ethanol (volume/volume); each blend of solvent is called a "test solvent". Three sets of six, 5 gram samples of Stevia starting material containing (i) 71.85% RA, 13.55% stevioside; (ii) 76.13% RA, 6.96% stevioside; and (iii) 81.58% rebaudioside A, 4.49% stevioside (the remainder in each consisted of various concentrations of dulcosides, rebaudiosides, and sterebin compounds) were prepared by blending two commercially available Stevia extracts, RA81.58 and RA40.27. All three sets of blends of Stevia starting material (each, a "Stevia blend") were dried in a blower oven at 80° C. overnight and were assumed to contain 0% moisture before processing.

5 grams of each Stevia blend were each placed in three sets of six, 100 ml glass round-bottomed flasks and 20 mls of each test solvent added, respectively, to the sets of flasks to create a 100Et/00W, 98Et/02W, 96Et/04W, 94Et/06W, 92Et/08W, and 90Et/10W "test mixtures" of each Stevia blend. The test mixtures were mixed at room temperature. With the exception of the 100Et/00W test mixtures, all of the Stevia starting material went into solution. Each test mixture was refluxed at 80° C. for 1 hour. Each test mixture was then cooled on ice for 1 hour. Each test mixture was then filtered over a Whatman GF/A glass microfiber filter (1.6 μm pore size). The solids from filtration of each test mixture ("first retentate") were collected and each first retentate mixed with a further 20 mls. of the same test solvent used for the first reflux of the corresponding test mixture to produce a "second test mixture". Each second test mixture was refluxed at 80° C. for one hour. Each second test mixture was than stored at 4° C. for 96 hours. Each second test mixture was then filtered over a Whatman GF/A glass microfiber filter to produce a retentate ("second retentate") of wet solids and each second retentate was dried in a blower oven at 80° C. until a constant weight was reached. Each gram of the dried second retentate from a given second test mixture was mixed with 4 mls of absolute ethanol in a 100 ml glass round-bottomed flask to create a "third test mixture". Each third test mixture was refluxed for one hour at 80° C. Each third test mixture was then filtered over a Whatman GF/A glass microfiber filter, the solids ("third retentate") collected and then dried in a blower oven at 80° C. until a constant weight was observed. To measure yield, the weight of each dried third retentate was determined. To measure purity, a 0.1 gram sample of each third retentate was analyzed for rebaudioside A and stevioside content using the HPLC Method described above.

Results:

Table 1, shows the effect of water content in test solvent on solids yield from RA71.85, RA76.13, and RA81.58 Stevia starting materials.

Figure 13:
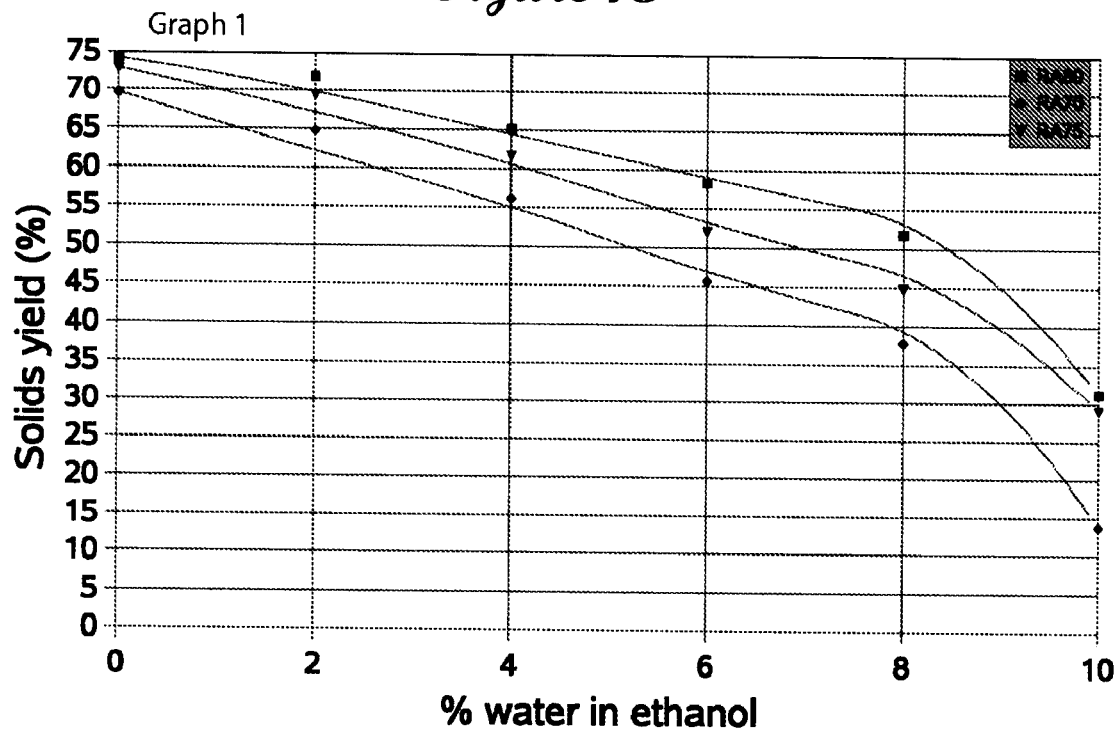
FIG. 13 shows Graph 1, which plots yield vs. water content of reflux solvent for different *Stevia* starting materials.

Graph 1 in FIG. 13 plots the effect of varying water content in test solvent on solids yield from RA71.85, RA76.13, and RA81.58 Stevia starting materials.

It can be seen from Table 1 that as the water content in the test solvent increased up to 8%, the solids yield declined gradually. However, when water content in the test solvent exceeded 8%, in all cases the solids yield declined significantly and at a much greater rate than with lower water contents. This suggests that to maintain yield with RA70 or higher Stevia starting material, the maximum water content should not exceed 8% by volume. Reb A yield was positively correlated to rebaudioside A content of the Stevia starting material: a higher initial Reb A content gave a higher solids yield in all test solvents. Moisture in Stevia starting material contributes to the total water content of a test solvent and will consequently have an effect on solids yield. Therefore, to control total water content in the text mixtures, all Stevia starting material was dried before formulating the test mixtures.

Table 2 shows the effect of water content in test solvent on Rebaudioside A purity from RA71.85, RA76.13, and RA81.58 Stevia starting materials.

Figure 14:
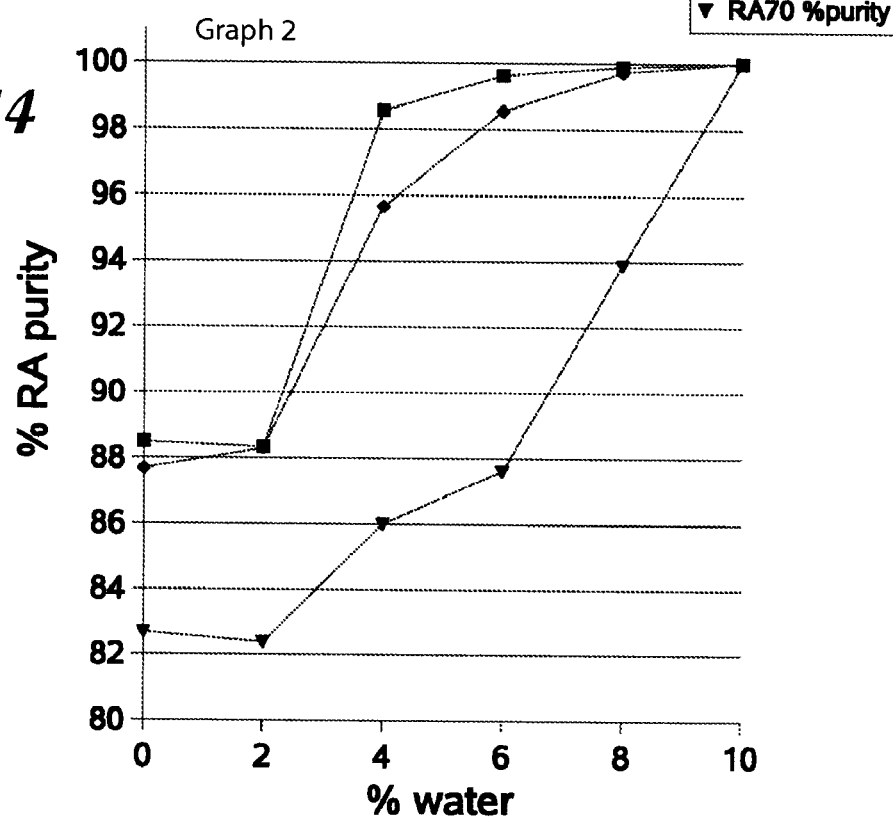
FIG. 14 shows Graph 2, which plots yield vs. water content of reflux solvent for different *Stevia* starting materials.

Graph 2 in FIG. 14 plots the effect of water content in test solvent on rebaudioside A purity from RA71.85, RA76.13, and RA81.58 Stevia starting materials.

It can seen from Table 2 and Graph 2 that Reb A purity of the final product generally increased with increasing water content in the test solvent. The exception was 2% water content, where there was either a decrease in Reb A purity or only a very small increase in Reb A purity compared with having no water in the test solvent. To obtain final product containing 99%+purity Reb A, Table 2 shows (bold figures) that for RA81.58 Stevia starting material, 6% moisture in the test solvent gave the desired 99+% Reb A purity with the highest yield. With RA76.13 Stevia starting material, 8% water content gave the desired 99+% Reb A purity with the highest yield. With RA71.85 Stevia starting material, 10% water content gave the desired 99+% Reb A purity with the highest yield. However, as shown by the data from Table 1, reaching the desired 99+% Reb A purity with lower quality Stevia starting material results in lower absolute yield.

Example 1 illustrates the need to empirically determine the optimal water content in the test solvent for each Stevia starting material used. These empirical observations led to the starting material assay and the reflux solvent approximation described above.

Example 2

Example 2. One reflux stage using a series of test solvents followed by a stirred wash stage.

Example 2 demonstrates that the second reflux in Example 1 can be eliminated and reflux with absolute ethanol can be replaced with a shorter duration stirred wash in absolute ethanol when using RA80 or higher *Stevia* starting material (if the *Stevia* starting material does not contain "stubborn" contaminants that require an additional reflux stage). The results of Example 2 show that using RA90, a single reflux stage and single wash stage typically produce 99+% purity Reb A.

In Example 2, as in Example 1, a series of six solvents was formulated containing 0%, 2%, 4%, 6%, 8%, and 10% water and the remaining percentage ethanol (volume/volume); each blend of solvent is called a "test solvent". 5 grams of RA89.95 *Stevia* starting material were placed in each of six 100 ml glass round-bottomed flasks and mixed with 20 mls of 100Et/00W, 98Et/02W, 96Et/04W, 94Et/06W, 92Et/08W, and 90Et/10W test solvents to create 100Et/00W, 98Et/02W, 96Et/04W, 94Et/06W, 92Et/08W, and 90Et/10W "test mixtures" of the *Stevia* starting material. With the exception of the 100Et/00W test mixture, all of the *Stevia* starting material went into solution. Each test mixture was refluxed at 80° C. for 1 hour. Each test mixture was then held at room temperature for 96 hours and then filtered over a Whatman GF/A glass microfiber filter (1.6 μm pore size). The solids in each test mixture ("prime retentate") were collected and each prime retentate mixed with 16 mls of absolute ethanol and stirred (stir bar) for 15 minutes at room temperature ("stirred wash"). The assumption was made that 20% (i.e., 1 gram) of the original solids remained in solution after the first reflux of Example 2 and 96 hour stand time, therefore 16 mls of EtOH solvent were use for each stirred wash to maintain the 1:4 mass to volume ratio of the test mixtures. After stirring, each test mixture was filtered over a Whatman GF/A glass microfiber filter and the solids ("stirred wash retentate") collected and then dried in a blower oven at 80° C. until the stirred wash retentates maintained a constant weight. Each dried, stirred wash retentate was weighed and a 0.1 g sample analyzed for rebaudioside A content using the HPLC Method described above.

Results:

Table 3 shows the final solids (dried, stirred wash retentate) weight, rebaudioside A recovery, and purity after a single EtOH reflux and stirred wash using RA89.95 *Stevia* starting material.

The method of Example 2 was repeated using RA81.67 *Stevia* starting material instead of RA89.95 *Stevia* starting material, ceteris paribus, with results shown in Table 4.

Table 4 shows the final solids (dried retentate from stirred wash stage) weights, rebaudioside A recovery, and Reb A purity after a single EtOH reflux and stirred wash using RA81.67 *Stevia* starting material. It can be seen in Table 3 that for higher quality *Stevia* starting material (RA90), a single EtOH reflux, followed by a short wash in absolute ethanol, is sufficient to obtain 100% pure Reb A final product. With higher quality *Stevia* starting material, there is no need for a second EtOH reflux or a reflux in absolute ethanol. A 15 minute wash in absolute ethanol is sufficient.

However, the same methodology (one EtOH reflux, one stirred wash) with approximately 10% lower Reb A purity *Stevia* starting material (i.e., RA80) does not result in a final product with rebaudioside A content greater than 96.24%. Moreover, the yield using RA80 *Stevia* starting material is approximately 10% less (Table 4). Therefore for lower quality *Stevia* starting material, it is necessary to use an additional reflux stage to produce 99+% purity Reb A.

Example 3

Example 3. One reflux stage, without stirred wash stage.

Example 3 demonstrates the effect of omitting the stirred wash stage on rebaudioside A purity of the final product.

In Example 3, two, 5 gram samples of RA89.95 *Stevia* starting material were placed in two 100 ml glass round-bottomed flasks, respectively, and each mixed with 20 mls of a 92Et/08W test solvent to form a test mixture (this experiment was conducted while the starting material assay was still being perfected). Each test mixture was refluxed for 1 hour at 80° C. Both test mixtures were left at room temperature for 96 hours and then filtered over a Whatman GF/A glass microfiber filter (1.6 μm pore size). The solids for each test mixture ("reflux retentate") were collected. One reflux retentate was dried in a blower oven at 80° C. ("non-stirred retentate") and the other reflux retentate was mixed with 16 mls of 100% ethanol, stirred (stir bar) for 15 minutes at room temperature, then filtered over a Whatman GF/A glass microfiber filter, and the solids ("stirred retentate") collected. The non-stirred retentate and the stirred retentate were dried in a blower oven at 80° C. until the retentates maintained a constant weight. 0.1 gram samples from both retentates were then analyzed for rebaudioside A content using the HPLC Method described above.

Results:

The dried, non-stirred retentate contained 96.32% rebaudioside A. The dried, stirred retentate contained 100% rebaudioside A. The 15 minute stirred wash step in absolute ethanol, in addition to a single EtOH reflux, is therefore necessary to obtain the desired 99+% Reb A purity of final product using an RA90 *Stevia* starting material.

Example 4

Example 4. Two reflux stages with ethanol purge and drying stage of industrial process in tandem with stirred wash stage of laboratory process.

Example 4 demonstrates that, using higher quality *Stevia* starting material, a 15 minute stirred wash in absolute ethanol is sufficient to obtain 99+% Reb A final product with desired solubility. In Example 4, RA89.95 *Stevia* starting material was processed through two reflux stages of the industrial embodiment of the invention, and a sample of the final product of the industrial process used as starting material in a stirred wash stage of the laboratory embodiment of the invention. Specifically, 100 kilograms of RA90 *Stevia* starting material were mixed with 400 liters of 90Et/10W solvent (this experiment was conducted while the starting material assay was still being perfected) and refluxed for 1 hour at 80° C., then cooled (chilled water in tank jacket) and allowed to stand for a minimum of 2 hours with mixture temperature maintained between 4° C. and 20° C. The mixture was filtered through a centrifugal decanter, and the retentate added to 400 liters of 90Et/10W solvent and refluxed for 1 hour at 80° C. The mixture from the second reflux was filtered through a centrifugal decanter. The retentate of the filtering of the second reflux mixture was mixed with water until the volume of the mixture was approximately twice the mass of the retentate (e.g., 350 kg retentate in a total mixture volume of 700 liters). The mixture in water was heated to 80° C. for approximately one hour to purge any residual ethanol from the mixture, then the mixture was spray-dried. There was no reflux in absolute ethanol prior to spray drying. The spray-dried product was weighed and a 0.1 gram sample was analyzed for rebaudioside A content using the HPLC Method described above. Five grams of the spray-dried material was mixed with 20 mls of absolute ethanol in a 100 ml round-bottomed flask and refluxed for 1 hour at 80° C. ("refluxed sample") and then allowed to cool to room temperature. A second 5 gram sample of the spray-dried material was mixed with 20 mls of absolute ethanol and stirred for 15 minutes at room temperature ("stirred sample"). Both samples were filtered over a Whatman GF/A glass fiber filter (1.6 µm pore size) and the retained solids of both samples were dried in a blower oven at 80° C. until the solids maintained a constant weight. 1 gram each of the refluxed sample and of the stirred sample were placed in 15 ml glass centrifuge tubes. Water was added to each tube in 0.1 ml increments and the mixture thoroughly shaken to ensure maximum solubilization. Incremental aliquots of water were added until complete solubilization was achieved as evidenced by the lack of any observable suspended solids in the solution. The final volume at which complete solubilization occurred in each sample was noted.

Results:

Table 5 shows the rebaudioside A purity and solids yield achieved using two reflux stages, with ethanol purge and drying stage, of the industrial embodiment of the invention.

Table 6 shows the solubility in water of the refluxed sample and of the stirred sample.

Using two reflux stages, in tandem with an ethanol purge and drying stage, of the industrial embodiment of the invention produced a 99.6% Reb A purity product. However, solubility of that product in water at room temperature was only 2%. This solubility may be useful for some commercial applications. The increased solubility (40%, at room temperature) afforded by the 1 hour reflux in absolute ethanol would meet the solubility requirements of most, if not all, commercial applications. It was found, however, that replacing the 1 hour reflux with a 15 minute stirred wash in absolute ethanol at room temperature resulted in a product with 33% solubility (at room temperature), which is acceptable for most commercial needs, including concentrates.

Example 5

Example 5. One reflux stage and stirred wash stage, with reduced standing times and without cooling.

Example 5 demonstrates the effects of a reduction in standing time and omission of cooling on purity and yield of rebaudioside A.

In Example 5, five, 5 gram samples of RA81.58 Stevia starting material and five, 5 gram samples of RA89.95 Stevia starting material were placed in two sets of five, 100 ml round-bottomed glass flasks, respectively, and each sample mixed with 20 mls of 92Et/08W solvent (each, a "test mixture"). The test mixtures were refluxed for 1 hour at 80° C. After the reflux, the five test mixtures in a given set were allowed to stand at room temperature (without stirring) for 0, 18, 24, 36, and 160 hours, one test mixture per set per standing time. Each test mixtures was filtered over a Whatman GF/A glass microfiber filter (1.6 µm pore size) and each retentate collected and mixed with 16 mls of absolute ethanol (each, a "test sample") and stirred (stir bar) at room temperature for 15 minutes. After the relevant standing time, a given test sample was then filtered over a Whatman GF/A glass microfiber filter and the retentate collected and dried at 80° C. until the solids maintained a constant weight. Each sample was then weighed and a 0.1 gram sample analyzed for Reb A content using the HPLC Method described above.

Results:

Table 7 shows yield and rebaudioside A purity of final product after various standing times.

For the RA81.58 purity Stevia starting material, a minimum standing time of 18 hours allowed maximum solids yield to be achieved. For the RA89.95 purity Stevia starting material, zero standing time produced 99+% purity Reb A final product. For lower RA purity Stevia starting material, increasing the standing time after a reflux stage increases the yield of final product (multiple refluxes are typically required to produce 99+% purity Reb A when using lower quality Stevia starting material).

Example 6

Example 6. One reflux stage and two stirred wash stages with ethanol purge and drying stage, industrial scale.

Example 6 demonstrates that a single reflux and two stirred washes, with spray drying, can produce 99+% purity rebaudioside A with acceptable water solubility at industrial scale when using lower quality Stevia starting material.

In Example 6, five hundred (500) kilograms of RA83.14 Stevia starting material were mixed with 2000 liters of 92Et/08W EtOH solvent and refluxed for 1 hour at 79° C., then cooled (chilled water in tank jacket) to 29° C. (elapsed time from end of reflux to start of decanting, 7 hrs., 15 min.). The cooled, refluxed mixture was filtered through a centrifugal decanter, and the retentate added to 1,600 liters of ethanol (retentate mass of 400 kg, 1:4 mass to volume ratio) at room temperature (29° C.) and stirred for 15 minutes (stirred wash stage). The stirred wash mixture was filtered through a centrifugal decanter, and the stirred wash stage was then repeated, i.e., the retentate from the centrifugal decanter was added to 1,600 liters of ethanol (1:4 mass to solvent ratio) at room temperature (29° C.) and stirred for 15 minutes (second stirred wash stage). The second stirred wash mixture was filtered through a centrifugal decanter, and the retentate was mixed with water until the volume of the mixture was approximately twice the mass of the retentate (e.g., 800 kg retentate in a total mixture volume of 1,600 liters). In the ethanol purge and drying step, the aqueous mixture was heated to 80° C. and maintained at that temperature for approximately ten hours to purge any residual ethanol from the mixture, then the mixture was spray-dried. Due to limited throughput of the spray dryer, the spray drying process required 6.5 hours. From the 500 kg of Stevia starting material, 302.3 kg of solids were recovered, or 60.46% of the Stevia starting material by dry weight. The 500 kg of Stevia starting material were RA83.14, i.e., contained 415.7 kg of Reb A. A recovery of 302.3 kg of solids represents a recovery of 72.3% of the Reb A in the Stevia starting material. The final product was 99.4% purity Reb A, determined using the HPLC Method described above. The solubility was 59.0% (at 25° C.).

Example 7

Example 7. Effect of varying ratio of solids weight to solvent volume on purity and yield.

Example 7 demonstrates the optional mass to solvent ratio analysis. Ten gram samples of oven-dried Stevia starting material containing 82.3% rebaudioside A were placed in each of five, 100 ml, glass, round-bottomed flasks and 20 mls, 30 mls, 40 mls, 50 mls, and 60 mls of 92Et/08W selected EtOH solvent were added, respectively, to each flask, which resulted in mass to solvent ratios of 1:2 through 1:6.

A magnetic stir bar was added to each flask and the mixtures refluxed for 1 hour at 80° C. with stirring. The samples were then cooled by placing them on ice for 1 hour. Each mixture was then filtered over a Whatman GF/A glass fiber filter. The wet solids retentate was then washed by adding 40 mls of 100% absolute ethanol and stirring at room temperature for 15 minutes. The mixture was then filtered over a Whatman GF/A glass fiber filter and the wet solids retentate dried at 80° C. in a blower oven. The resulting dried solids were then weighed and analyzed by the HPLC method, as described above, for rebaudioside A content.

A duplicate set of five, 100 ml, glass, round-bottomed flasks, each containing 10 grams of RA82.3 Stevia starting material and the respective volumes of 92Et/08W solvent described above per flask, were similarly mixed and refluxed for 1 hour at 80° C., cooled, then filtered. The wet solids retentate was placed back in the set of five, 100 ml, glass, round-bottomed flasks and the respective volumes of 92Et/08W solvent per flask added and mixed as described above. The mixtures were refluxed for 1 hour at 80° C., cooled, filtered, and then washed in 40 mls of absolute ethanol. Each wash mixture was then filtered and the resulting wet solids retentate dried in a blower oven at 80° C. The dried solids were weighed and analyzed by the HPLC method described above for rebaudioside A content.

Table 7 below shows the yield and purity data obtained for each sample that was processed using one reflux stage and a stirred wash stage.

TABLE 7

Using 92Et/08W selected EtOH solvent

| Number of Refluxes/<br>Mass:Solvent Ratio | % Reb A | % Solids Yield | % Reb A Yield |
|---|---|---|---|
| 1 Reflux/1:2 ratio | 88.88 | 79.7 | 70.8 |
| 1 Reflux/1:3 ratio | 90.85 | 79.7 | 72.4 |
| 1 Reflux/1:4 ratio | 93.67 | 78.6 | 73.6 |
| 1 Reflux/1:5 ratio | 96.51 | 74.8 | 72.2 |
| 1 Reflux/1:6 ratio | 97.15 | 72.8 | 70.7 |

Table 8 below shows the yield and purity data obtained for each sample that was processed using two reflux stages and a stirred wash stage.

TABLE 8

Using 92Et/08W selected EtOH solvent

| Number of Refluxes/<br>Mass:Solvent Ratio | % Reb A | % Solids Yield | % Reb A Yield |
|---|---|---|---|
| 2 Refluxes/1:2 ratio | 92.74 | 65.3 | 60.6 |
| 2 Refluxes/1:3 ratio | 97.42 | 62.4 | 60.8 |
| 2 Refluxes/1:4 ratio | 99.17 | 59.9 | 59.4 |
| 2 Refluxes/1:5 ratio | 99.03 | 56.1 | 55.6 |
| 2 Refluxes/1:6 ratio | 100.00 | 51.9 | 52.2 |

During the experimental procedure described above, it was noted that using a mass to solvent ratio of less than 1:4 resulted in solidification of the mixture in the flask after reflux. Using a ratio of less than 1:4 on an industrial scale would therefore significantly hamper transfer of material from a mixing tank after reflux. It can be seen from Table 7 above that while a single reflux and stirred wash generally raised rebaudioside A purity, even a 1:6 mass to solvent ratio (m/v) was not sufficient to obtain a final product of 99%+ purity Reb A using this particular RA82.3 Stevia starting material. In addition, with the single reflux and stirred wash, solids yield declined only 7.1% as the ratio of mass to solvent ratio increased 3-fold. Reb A yield did not appear to change linearly with the increasing ratio of solids mass to reflux solvent. This suggests that increasing the amount of reflux solvent does not simply dilute the sample and allow a directly proportionate increase in the amount of solids remaining in solution after reflux, but that the chemical interactions during reflux, which allow for preferential precipitation of Reb A, are more directly linked to the ratio of water to ethanol in the selected EtOH solvent, as shown in Examples 1 and 2.

Table 8 shows the results obtained using RA82.3 Stevia starting material, two refluxes, and a stirred wash. Rebaudioside A purity in the final product only exceeded 99% when a ratio of 1:4 or higher was used. Solid recovery dropped 13.4% as the mass to solvent ratio (m/v) increased threefold. This drop in yield was approximately twice that seen with a single reflux and single stirred wash, which reflects the use of an additional reflux stage. In addition, rebaudioside A yield dropped 8.4% over the range of mass to solvent ratios used (1:2 through 1:6. (m/v)). Notably, a 1:6 mass to solvent ratio gave a 100% pure rebaudioside A final product from an RA82.3 Stevia starting material.

Based upon the data in Example 7, a minimum 1:4 mass to solvent (m/v) ratio is preferred for a target purity of 99+% Reb A. Higher mass to solvent ratios can be used, but the increased cost in terms of total solvent consumed, and heating and cooling larger mixing tanks, must be balanced against the desired target purity. Example 7 also shows that two reflux stages and an ethanol purge and drying stage was required to obtain 99+% purity Reb A product using this particular lower quality Stevia starting material.

The experience in Example 6 of obtaining 99+% purity Reb A final product using RA83.14 Stevia starting material, a single reflux, and two stirred washes, compared with two reflux stages and single stirred wash stage required in Example 7 using RA82.3 Stevia starting material, illustrates the importance of the EtOH formulation stage, with optional mass to solvent ratio assay, in process optimization (usually, maximizing Reb A yield at 99+% purity final product while minimizing processing costs).

Example 8

Example 8 demonstrates processing an RA82.3 Stevia starting material (the same batch as used in Example 7) using one reflux stage, in conjunction with two stirred wash stages in which the mass to solvent ratio is varied.

To determine the effect of varying the solvent ratio in two stirred wash stages following a single reflux stage, 10 gram samples of RA82.3 Stevia starting material were placed in each of four, 100 ml round-bottomed flasks (magnetic stir bar added). 40 mls of 92Et/08W were added to each flask of the four flasks and the mixtures stirred to dissolve solids. Each mixture was refluxed for 1 hour at 80° C. with stirring. After reflux, each mixture was placed on ice for 1 hour and then filtered over Whatman GF/A glass microfiber filter paper. The wet solids retentate from each mixture was placed in a 100 ml round-bottomed flask (magnetic stir bar added) with 30 mls, 40 mls, 50 mls, or 60 mls, respectively, of 100% ethanol and stirred with a magnetic stirrer at room temperature for 15 minutes. Each mixture then filtered over Whatman GF/A glass microfiber filter paper to produce four samples of wet solids retentate. A small sample (approximately 0.1 gram) of each sample was dried in a blower oven at 80° C. until a constant weight was reached and then analyzed for rebaudioside A content using the HPLC Method described above. The remaining wet solids retentate from each mixture was placed in a 100 ml round-bottomed flask (magnetic stir bar added) with 30 mls, 40 mls, 50 mls, or 60 mls, respectively, of 100% ethanol and stirred with a magnetic stirrer at room temperature for 15 minutes. Finally, each mixture was filtered, and the wet solids retentate of each sample dried at 80° C. until a constant weight was reached. Each sample of dried solid was weighed and a sample of the dried solids assayed for rebaudioside A content using the HPLC Method described above.

TABLE 9

| Number of Refluxes/ Mass:Solvent Ratio | % Reb A | % Solids Yield | % Reb A Yield |
| --- | --- | --- | --- |
| 1 reflux 1:4, 1 wash 1:3 | 89.90 | nd* | nd* |
| 1 reflux 1:4, 1 wash 1:4 | 89.28 | nd* | nd* |
| 1 reflux 1:4, 1 wash 1:5 | 90.74 | nd* | nd* |
| 1 reflux 1:4, 1 wash 1:6 | 92.85 | nd* | nd* |
| 1 reflux 1:4, 2 washes 1:3 | 95.25 | 64.4 | 74.54 |
| 1 reflux 1:4, 2 washes 1:4 | 96.99 | 64.2 | 75.66 |
| 1 reflux 1:4, 2 washes 1:5 | 95.01 | 64.0 | 73.88 |
| 1 reflux 1:4, 2 washes 1:6 | 95.16 | 63.7 | 73.65 |

*no data

Based on the data in Table 9, inclusion of a second wash step raised the final rebaudioside A purity between 2.3 and 7.7%, with the largest increase in purity seen with an additional 1:4 (mass to solvent ratio) wash. However, the target product of 99+% purity Reb A was not obtained using a single reflux and two stirred washes, regardless of the mass to solvent ratio in the stirred wash stages. The final purities after the second stirred wash stage, regardless of the ratio used, only varied by 1.98%. This suggests that simply raising the mass to solvent ratio in the stirred wash stage(s) does not have a significant effect on raising Reb A purity. Similarly, yield was not significantly affected by the increasing the mass to solvent ratio in the stirred wash stages.

Example 9

Example 9 demonstrates processing an RA82.3 *Stevia* starting material (the same batch as used in Example 7) using two reflux stages in which the mass to solvent ratio was varied, in conjunction with a final stirred wash stage (1:4 mass to solvent ratio).

To determine the effect of varying the solvent ratio in two reflux stages, a 10 gram sample of RA82.3 *Stevia* starting material was placed each of eleven, 100 ml round-bottomed flasks (magnetic stir bar added). To three of the eleven flasks, 40 mls of 92Et/08W solvent were added (collectively, the "4x/ series"), respectively, to the flasks and the mixtures stirred to dissolve solids. To four of the eleven flasks, 50 mls of 92Et/08W solvent were added (collectively, the "5x/ series"), respectively, to the flasks and the mixtures stirred to dissolve solids. To the remaining four of the eleven flasks, 60 mls of 92Et/08W solvent were added (collectively, the "6x/ series"), respectively, to the flasks and the mixtures stirred to dissolve solids. Each mixture was refluxed for 1 hour at 80° C. with stirring. After reflux, each mixture was placed on ice for 1 hour and then filtered over Whatman GF/A glass microfiber filter paper. The wet solids retentate in the three samples in the 4x/ series was mixed with 40 mls, 50 mls, or 60 mls, respectively, of 92Et/08W solvent and the samples refluxed for a second time at 80° C. with stirring. The wet solids retentate in the four samples in the 5x/ series was mixed with 30 mls, 40 mls, 50 mls, or 60 mls, respectively, of 92Et/08W solvent and the samples refluxed for a second time at 80° C. with stirring. The wet solids retentate in the four samples in the 6x/ series was mixed with 30 mls, 40 mls, 50 mls, or 60 mls, respectively, of 92Et/08W solvent and the samples refluxed for a second time at 80° C. with stirring. Each mixture was placed on ice for 1 hour and then filtered over Whatman GF/A glass microfiber filter paper. Finally, the wet solids retentate of each sample was mixed with 40 mls of absolute ethanol and stirred for 15 minutes at room temperature, then filtered over Whatman GF/A glass microfiber filter paper. The wet solids retentate from each sample was then dried to a constant weight at 80° C. in a blower oven. All samples were then weighed and analyzed for rebaudioside A using the HPLC Method described above.

TABLE 10

| Sample* | % RA | % Solids yield | % RA yield |
| --- | --- | --- | --- |
| 4x/4x | 100 | 58.6 | 71.26 |
| 4x/5x | 100 | 56.7 | 68.85 |
| 4x/6x | 99.5 | 44.7 | 53.99 |
| 5x/3x | 99.3 | 49.0 | 59.12 |
| 5x/4x | 99.9 | 60.2 | 73.03 |
| 5x/5x | 99.9 | 48.7 | 59.10 |
| 5x/6x | 100 | 56.9 | 69.14 |
| 6x/3x | 99.0 | 53.4 | 64.29 |
| 6x/4x | 98.4 | 60.3 | 72.10 |
| 6x/5x | 100 | 46.2 | 56.10 |
| 6x/6x | 100 | 42.9 | 52.10 |

*"4x/4x" means a first reflux stage using a mass to solvent ratio of 1:4 followed by a second reflux stage using a mass to solvent ratio of 1:4; "4x/5x" means a first reflux stage using a mass to solvent ratio of 1:4 followed by a second reflux stage using a mass to solvent ratio of 1:5; and so on. In all samples, the second reflux stage was followed by a stirred wash stage.

The data in Table 10 shows that varying the mass to solvent ratio in each of two reflux steps did not have a large effect on purity, with virtually all final products reaching the desired target purity of 99+% purity Reb A. However, when solids yield was taken into account, the rebaudioside A recovery was affected by varying the ratio. The samples processed using 1:4 and 1:4, and 1:5 and 1:4, mass to solvent ratios gave the highest recovery of rebaudioside A at the target purity of 99+% purity Reb A. Therefore, the most economical means of achieving maximum yield and target purity is by using a first reflux stage with a mass to solvent ratio of 1:4 followed by a second reflux stage with a mass to solvent ratio of 1:4.

We claim:

1. A method of purifying rebaudioside A from *Stevia* starting material comprising: (i) formulating a selected EtOH solvent consisting of water and ethanol, (ii) performing a first reflux stage by refluxing the *Stevia* starting material in the selected EtOH solvent and optionally performing additional reflux stages using retentate isolated from a refluxed mixture or from a stirred wash mixture, (iii) optionally, performing one or more stirred wash stages, and (iv) performing an ethanol purge and drying stage, wherein formulating a selected EtOH solvent comprises either (A) a reflux solvent approximation, wherein, based on the asserted or labeled purity of a batch of *Stevia* starting material, for a *Stevia* starting material labeled or asserted to be 90% rebaudioside A purity, the reflux solvent is formulated as ethanol and water, and for every 5% decrease in rebaudioside A purity below 90% rebaudioside A purity in the *Stevia* starting material, based on the asserted or labeled purity of a batch of *Stevia* starting material, increasing the water content of reflux solvent 1% above a baseline of 6% water, and the remaining volume of the reflux solvent is ethanol, or (B) preparing a series of test mixtures in which the water content is uniformly incremented from 0.5% to 15%, or within a subset of that 0.5% to 15% range, and the balance of solvent in each such test mixture is ethanol, assaying the retentate of a reflux of the *Stevia* starting material in each test mixture for rebaudioside A purity, and selecting as the selected EtOH solvent the test mixture that produces a retentate with the highest purity rebaudioside A.

2. A method of purifying rebaudioside A from *Stevia* starting material comprising:

Formulating a selected EtOH solvent consisting of water and ethanol for the *Stevia* starting material;

Mixing and refluxing the *Stevia* starting material in the selected EtOH solvent to create a refluxed mixture;

Separating a retentate by filtering the refluxed mixture;

Mixing and stirring the retentate in ethanol to create a stirred wash mixture;

Separating a retentate by filtering the stirred wash mixture; and

Purging the ethanol and drying the retentate, wherein the dried retentate is rebaudioside A, wherein formulating a selected EtOH solvent for the *Stevia* starting material comprises either (A) a reflux solvent approximation, wherein, based on the asserted or labeled purity of a batch of *Stevia* starting material, for a *Stevia* starting material labeled or asserted to be 90% rebaudioside A purity, the reflux solvent is formulated as ethanol and water, and for every 5% decrease in rebaudioside A purity below 90% rebaudioside A purity in the *Stevia* starting material, based on the asserted or labeled purity of a batch of *Stevia* starting material, increasing the water content of reflux solvent 1% above a baseline of 6% water, and the remaining volume of the reflux solvent is ethanol, or (B) preparing a series of test mixtures in which the water content is uniformly incremented from 0.5% to 15%, or within a subset of that 0.5% to 15% range, and the balance of solvent in each such test mixture is ethanol, assaying the retentate of a reflux of the *Stevia* starting material in each test mixture for rebaudioside A purity, and selecting as the selected EtOH solvent the test mixture that produces a retentate with the highest purity rebaudioside A.

3. A method of purifying rebaudioside A from *Stevia* starting material comprising:

Formulating a selected EtOH solvent consisting of water and ethanol for the *Stevia* starting material;

Mixing and refluxing the *Stevia* starting material in the selected EtOH solvent to create a refluxed mixture;

Separating a retentate by filtering the refluxed mixture, and optionally mixing and stirring the retentate in ethanol to create a stirred wash mixture and separating a retentate by filtering the stirred wash mixture;

Mixing and refluxing the retentate in the selected EtOH solvent to create a refluxed mixture;

Separating a retentate by filtering the refluxed mixture, and optionally mixing and stirring the retentate in ethanol to create a stirred wash mixture and separating a retentate by filtering the stirred wash mixture;

Optionally repeating one or more times the preceding two steps; and

Purging the ethanol and drying the retentate, wherein the dried retentate is rebaudioside A, wherein formulating a selected EtOH solvent for the *Stevia* starting material comprises either (A) a reflux solvent approximation, wherein, based on the asserted or labeled purity of a batch of *Stevia* starting material, for a *Stevia* starting material labeled or asserted to be 90% rebaudioside A purity, the reflux solvent is formulated as ethanol and water, and for every 5% decrease in rebaudioside A purity below 90% rebaudioside A purity in the *Stevia* starting material, based on the asserted or labeled purity of a batch of *Stevia* starting material, increasing the water content of reflux solvent 1% above a baseline of 6% water, and the remaining volume of the reflux solvent is ethanol, or (B) preparing a series of test mixtures in which the water content is uniformly incremented from 0.5% to 15%, or within a subset of that 0.5% to 15% range, and the balance of solvent in each such test mixture is ethanol, assaying the retentate of a reflux of the *Stevia* starting material in each test mixture for rebaudioside A purity, and selecting as the selected EtOH solvent the test mixture that produces a retentate with the highest purity rebaudioside A.

4. The method of claim 1, 2, or 3, wherein the method of mixing and refluxing the *Stevia* starting material comprises:

Mixing 1 part by mass of *Stevia* starting material with from 3 to 10 parts by volume, more preferably from 4 to 6 parts by volume, and most preferably approximately 4 parts by volume of the selected EtOH solvent to create a reflux mixture; and Refluxing the reflux mixture in an appropriate apparatus at approximately the boiling point of ethanol for approximately one hour.

5. The method of claim 1 or 3, wherein the method of mixing and refluxing the retentate in one or more additional refluxes comprises:

Mixing 1 part by mass of the retentate with from 3 to 10 parts by volume, more preferably from 4 to 6 parts by volume, and most preferably approximately 4 parts by volume of the selected EtOH solvent to create a reflux mixture; and Refluxing the reflux mixture in an appropriate apparatus at approximately the boiling point of ethanol for approximately one hour.

6. The method of claim 1, 2, or 3, wherein the method of separating retentate by filtering the refluxed mixture or stirred wash mixture comprises:

Filtering the mixture using a filtering means appropriate for the volume of refluxed mixture and throughput required and that separates particles with an axis or diameter approximately greater than 2.0 μm, more preferably greater than 1.5 μm; and most preferably equal to or greater than 0.1 μm; and Collecting the separated particles from the filtering means.

7. The method of claim 1, 2, or 3, wherein the method of mixing and stirring in a stirred wash retentate from a previous step and separating retentate by filtering the stirred wash mixture comprises:

Mixing 1 part by mass of the isolated rebaudioside A with from 3 to 10 parts by volume, more preferably from 4 to 6 parts by volume, and most preferably approximately 4 parts by volume of ethanol to create a wash mixture;

Stirring the wash mixture in an appropriate apparatus for approximately fifteen minutes;

Filtering the wash mixture using a filtering means appropriate for the volume of refluxed mixture and throughput required and that separates particles with an axis or diameter approximately greater than 2.0 μm, more preferably greater than 1.5 μm; and most preferably equal to or greater than 0.1 μm; and Collecting the separated particles from the filtering means.

8. The method of claim 1, 2, or 3, wherein the method of purging the ethanol and drying the isolated rebaudioside A comprises, in a laboratory embodiment of the invention, drying the isolated rebaudioside A is an oven, preferably a blower oven, at or above 79° C., and, in an industrial embodiment, of the invention:

Mixing 1 part by mass of retentate, isolated in a preceding step by filtering a refluxed mixture or a stirred wash mixture, with water such that the ultimate mixture volume is approximately twice the mass of the retentate;

Heating the mixture in a vented vessel to at least 79° C. while stirring;

Stirring the mixture until the ethanol content of the mixture is equal to or less than the maximum ethanol content permitted by an associated spray dryer;

Feeding the mixture to the spray dryer; and

Collecting the dried rebaudioside A.

9. The method of claim 1, 2, or 3, wherein ethanol used in formulating the EtOH solvent and in the selected EtOH solvent is either absolute ethanol or denatured ethanol.

10. The method of claim 1, 2, or 3, wherein an alkanol other than ethanol is used in place of ethanol in the selected EtOH solvent.

11. The method of claim 1, 2, or 3, wherein an alkanol is used in place of ethanol in the selected EtOH solvent and in any stirred wash stages.

12. The method of claim 1, 2, or 3, wherein a first alkanol is used in the selected EtOH solvent, and a second alkanol is used in any stirred wash stages.

13. The method of claim 1, 2, or 3, wherein the method of formulating the selected EtOH solvent includes a mass to volume ratio assay.

14. A method of purifying rebaudioside A from *Stevia* starting material comprising: (i) formulating a selected EtOH solvent consisting of water and ethanol, (ii) performing a first reflux stage by refluxing the *Stevia* starting material in the selected EtOH solvent and optionally performing additional reflux stages using retentate isolated from a refluxed mixture or from a stirred wash mixture, (iii) optionally, performing one or more stirred wash stages, and (iv) performing an ethanol purge and drying stage, wherein formulating a selected EtOH solvent comprises preparing a series of test mixtures in which the water content is uniformly incremented from 0.5% to 15%, or within a subset of that 0.5% to 15% range, and the balance of solvent in each such test mixture is ethanol, assaying the retentate of a reflux of the *Stevia* starting material in each test mixture for rebaudioside A purity and yield, and selecting as the selected EtOH solvent the test mixture that produces a retentate with the highest yield of rebaudioside A final product that has a rebaudioside A purity acceptable to the user.

15. A method of purifying rebaudioside A from *Stevia* starting material comprising:

Formulating a selected EtOH solvent consisting of water and ethanol for the *Stevia* starting material;

Mixing and refluxing the *Stevia* starting material in the selected EtOH solvent to create a refluxed mixture;

Separating a retentate by filtering the refluxed mixture;

Mixing and stirring the retentate in ethanol to create a stirred wash mixture;

Separating a retentate by filtering the stirred wash mixture; and

Purging the ethanol and drying the retentate, wherein the dried retentate is rebaudioside A, wherein formulating a selected EtOH solvent for the *Stevia* starting material comprises preparing a series of test mixtures in which the water content is uniformly incremented from 0.5% to 15%, or within a subset of that 0.5% to 15% range, and the balance of solvent in each such test mixture is ethanol, assaying the retentate of a reflux of the *Stevia* starting material in each test mixture for rebaudioside A purity and yield, and selecting as the selected EtOH solvent the test mixture that produces a retentate with the highest yield of rebaudioside A final product that has a rebaudioside A purity acceptable to the user.

16. A method of purifying rebaudioside A from *Stevia* starting material comprising:

Formulating a selected EtOH solvent consisting of water and ethanol for the *Stevia* starting material;

Mixing and refluxing the *Stevia* starting material in the selected EtOH solvent to create a refluxed mixture;

Separating a retentate by filtering the refluxed mixture, and optionally mixing and stirring the retentate in ethanol to create a stirred wash mixture and separating a retentate by filtering the stirred wash mixture;

Mixing and refluxing the retentate in the selected EtOH solvent to create a refluxed mixture;

Separating a retentate by filtering the refluxed mixture, and optionally mixing and stirring the retentate in ethanol to create a stirred wash mixture and separating a retentate by filtering the stirred wash mixture;

Optionally repeating one or more times the preceding two steps; and

Purging the ethanol and drying the retentate, wherein the dried retentate is rebaudioside A, wherein formulating a selected EtOH solvent for the *Stevia* starting material comprises preparing a series of test mixtures in which the water content is uniformly incremented from 0.5% to 15%, or within a subset of that 0.5% to 15% range, and the balance of solvent in each such test mixture is ethanol, assaying the retentate of a reflux of the *Stevia* starting material in each test mixture for rebaudioside A purity and yield, and selecting as the selected EtOH solvent the test mixture that produces a retentate with the highest yield of rebaudioside A final product that has a rebaudioside A purity acceptable to the user.

17. The method of claim 14, 15, or 16, wherein the method of formulating the selected EtOH solvent includes a mass to volume ratio assay.

18. The method of claim 14, 15, or 16, wherein the method of mixing and refluxing the *Stevia* starting material comprises:

Mixing 1 part by mass of *Stevia* starting material with from 3 to 10 parts by volume of the selected EtOH solvent to create a reflux mixture; and Refluxing the reflux mixture in an appropriate apparatus at approximately the boiling point of ethanol for approximately one hour.

19. The method of claim 14 or 16, wherein the method of mixing and refluxing the retentate in one or more additional refluxes comprises:

Mixing 1 part by mass of the retentate with from 3 to 10 parts by volume of the selected EtOH solvent to create a reflux mixture; and Refluxing the reflux mixture in an appropriate apparatus at approximately the boiling point of ethanol for approximately one hour.

20. The method of claim 14, 15, or 16, wherein the method of separating retentate by filtering the refluxed mixture or stirred wash mixture comprises:

Filtering the mixture using a filtering means appropriate for the volume of refluxed mixture and throughput required and that separates particles with an axis or diameter approximately equal to or greater than 0.1 µm; and Collecting the separated particles from the filtering means.

21. The method of claim 14, 15, or 16, wherein the method of mixing and stirring in a stirred wash retentate from a previous step and separating retentate by filtering the stirred wash mixture comprises:
- Mixing 1 part by mass of the isolated rebaudioside A with from 3 to 10 parts by volume of ethanol to create a wash mixture;
- Stirring the wash mixture in an appropriate apparatus for approximately fifteen minutes;
- Filtering the wash mixture using a filtering means appropriate for the volume of refluxed mixture and throughput required and that separates particles with an axis or diameter approximately equal to or greater than 0.1 μm; and
- Collecting the separated particles from the filtering means.

22. The method of claim 14, 15, or 16, wherein the method of purging the ethanol and drying the isolated rebaudioside A comprises, in a laboratory embodiment of the invention, drying the isolated rebaudioside A is an oven, preferably a blower oven, at or above 79° C., and, in an industrial embodiment, of the invention:
- Mixing 1 part by mass of retentate, isolated in a preceding step by filtering a refluxed mixture or a stirred wash mixture, with water such that the ultimate mixture volume is approximately twice the mass of the retentate;
- Heating the mixture in a vented vessel to at least 79° C. while stirring;
- Stirring the mixture until the ethanol content of the mixture is equal to or less than the maximum ethanol content permitted by an associated spray dryer;
- Feeding the mixture to the spray dryer; and
- Collecting the dried rebaudioside A.

23. The method of claim 14, 15, or 16, wherein ethanol used in formulating the EtOH solvent and in the selected EtOH solvent is either absolute ethanol or denatured ethanol.

24. The method of claim 14, 15, or 16, wherein an alkanol other than ethanol is used in place of ethanol in the selected EtOH solvent.

25. The method of claim 14, 15, or 16, wherein an alkanol is used in place of ethanol in the selected EtOH solvent and in any stirred wash stages.

26. The method of claim 14, 15, or 16, wherein a first alkanol is used in the selected EtOH solvent, and a second alkanol is used in any stirred wash stages.

* * * * *